United States Patent
Fleming et al.

(10) Patent No.: US 11,305,019 B2
(45) Date of Patent: Apr. 19, 2022

(54) FUNCTIONALIZED NUCLEIC ACID NANOSTRUCTURES FOR RNA DELIVERY

(71) Applicants: Guild BioSciences, Dublin, OH (US); Ian Fleming, Hilliard, OH (US); Xi Chun Zhou, Littleton, CO (US)

(72) Inventors: Ian Fleming, Hilliard, OH (US); Xi Chun Zhou, Littleton, CO (US)

(*) Notice: Subject to any disclaimer, the term of this patent is extended or adjusted under 35 U.S.C. 154(b) by 0 days.

(21) Appl. No.: 16/318,462

(22) PCT Filed: Jul. 20, 2017

(86) PCT No.: PCT/US2017/043027
§ 371 (c)(1),
(2) Date: Jan. 17, 2019

(87) PCT Pub. No.: WO2018/017806
PCT Pub. Date: Jan. 25, 2018

(65) Prior Publication Data
US 2019/0240340 A1   Aug. 8, 2019

Related U.S. Application Data

(60) Provisional application No. 62/364,427, filed on Jul. 20, 2016.

(51) Int. Cl.
| | |
|---|---|
| *A61K 47/54* | (2017.01) |
| *A61K 9/00* | (2006.01) |
| *A61K 31/713* | (2006.01) |
| *A61K 47/64* | (2017.01) |
| *C12N 15/113* | (2010.01) |
| *A61K 38/00* | (2006.01) |

(52) U.S. Cl.
CPC ......... *A61K 47/549* (2017.08); *A61K 9/0092* (2013.01); *A61K 31/713* (2013.01); *A61K 47/64* (2017.08); *C12N 15/113* (2013.01); *A61K 38/00* (2013.01); *C12N 2310/14* (2013.01); *C12N 2310/3519* (2013.01); *C12N 2320/32* (2013.01)

(58) Field of Classification Search
CPC .... A61K 38/00; A61K 31/713; A61K 47/549; A61K 47/64; A61K 31/7088; A61K 9/0092
See application file for complete search history.

(56) References Cited

U.S. PATENT DOCUMENTS

2016/0082122 A1   3/2016   Bachelet et al.

FOREIGN PATENT DOCUMENTS

WO   2014170899 A1   10/2014

OTHER PUBLICATIONS

Liu et al.,"Triple negative breast cancer therapy with CDK1 siRNA delivered by cationic lipid assisted PEG-PLA nanoparticles", Journal of Controlled Release, 2014, pp. 114-121 (Year: 2014).*
Yan et al., "Growth and Origami Folding of DNA on Nanoparticles for High-Efficiency Molecular Transport in Cellular Imaging and Drug Delivery", Angew. Chew. Int. Ed, 2015, pp. 2431-2435 (Year: 2015).*
Lee et al., "Molecularly self-assembled nucleic acid nanoparticle for targeted in vivo siRNA delivery", Nature Nanotechnology, 2012, pp. 389-393 (Year: 2012).*
Smith et al., Nucleic Acid Nanostructures for Biomedical Applications, Nanomedicine, (Jan. 1, 2013), vol. 8, No. 1, pp. 105-121.

* cited by examiner

*Primary Examiner* — Lianko G Garyu
(74) *Attorney, Agent, or Firm* — Edward E. Sowers; Brannon Sowers & Cracraft PC

(57) ABSTRACT

The present disclosure provides cell-penetrating nucleic acid nanostructures well suited as transfection reagents for the delivery of bioactive agents to cells both in vivo and in vitro for research, diagnostic, and/or therapeutic purposes.

20 Claims, 6 Drawing Sheets

Specification includes a Sequence Listing.

_ FUNCTIONALIZED NUCLEIC ACID NANOSTRUCTURES FOR RNA DELIVERY

CROSS-REFERENCE TO RELATED APPLICATIONS

This application claims priority to PCT Patent Application No. PCT/US17/43027, filed Jul. 20, 2017, which claims benefit of U.S. Provisional Patent Application No. 62/364,427, filed Jul. 20, 2016, which are incorporated by reference herein.

GOVERNMENT RIGHTS

This invention was made with government support under NIH Grant Number 1R43GM113569-01, titled "Functionalized DNA origami nanostructures for siRNA delivery". The U.S. Government has certain rights in the invention.

SEQUENCE LISTING

The instant application contains a Sequence Listing which has been submitted electronically in ASCII format and is hereby incorporated by reference in its entirety. Said ASCII copy, created on Mar. 25, 2021, is named 254-14350_SL.txt and is 55,697 bytes in size.

BACKGROUND

DNA origami is a method through which single-stranded DNA can be systematically folded into complex and molecularly defined two- and three-dimensional nanostructures using oligonucleotide hybridization and inter-strand cross-overs to dictate the final shape. In the last 10 years, this technique has proven utility in applications including cellular imaging, drug delivery, bio-sensing and nano-mechanics through proper functionalization of DNA origami with aptamers, antibodies, enzymes, and fluorescent dyes. Important biological properties of DNA origami nanostructures include defined dimensions and shape which can be established through the programmed routing of oligonucleotide staples within the single-stranded scaffold DNA, as well as the biocompatible nature of DNA material. The use of DNA origami nanostructures in drug delivery has already proven effective for specific and tunable release or killing of cancer cells.

Intracellular delivery of small interfering RNA (siRNA) for gene silencing, which can be used to manipulate cellular phenotypes and as a therapy, is a challenging task. Current methods are often mediated by micelle type structures composed of synthetic and semi-synthetic polymers with cationic properties to encapsulate the siRNA for cellular internalization, which have two inherent disadvantages in the methods used to transport negatively charged RNA across the lipid bilayer: increased membrane permeability and immunotoxicity. The optimal delivery system needs to encompass highly efficient cell uptake, low cytotoxicity and immunotoxicity, high biocompatibility, include targeting moieties for in vivo spatiotemporal delivery and exhibit low off-target effects.

Methods to enhance the delivery of therapeutics have incorporated ligands for cell-specific receptor-mediated entry and cell penetrating peptides for improved, but generally non-specific, entry. Receptor targeted drug delivery takes advantage of receptors for small molecules and proteins such as vitamins, antibodies, transferrin, growth factors and aptamers which may be present only on a subset of cell types. Tailoring the targeting ligand for the disease of interest is an important step in cell-specific receptor-mediated delivery. In cancer targeted therapies, folic acid and HER2 are two well established ligands for cell uptake. Cell penetrating peptides (CPP) are emerging as an alternative to ligand mediated entry because CPPs generally enter in a noninvasive manner and do not compromise the integrity of cell membranes. Hundreds of CPPs have been described composed of both naturally occurring and synthetic sequences. The sequence identity of each CPP appears to be what dictates its method and efficiency of entry with peptides entering both endocytic and direct penetration pathways. Delivery of siRNA duplexes by reductive release from carriers such as dendrimers, poly-D-arginine, folate-PEG, copolymers, CPPs and DNA has been demonstrated previously.

SUMMARY

A functionalized 24 helix bundle DNA origami nanostructure (CPP-DON) can be efficiently assembled in a one-pot reaction with cell penetrating peptides and subsequently conjugated with siRNAs as an effective transfection reagent. In one example, a CPP-DON-siRNA nanostructure is internalized by HeLa cells and siRNA duplexes attached by disulfide bonds are released following cellular uptake in the reductive intracellular milieu to silence gene expression in human cells. One targeting approach has used folic acid because its specific receptor is not expressed on healthy cells, but is abundant on the surface of cancer cells. In addition to folic acid, three other widely used CPPs (Penetratin, MAP, Hph-1) were used to study the efficiency of DNA origami internalization by human cells. Findings demonstrate that CPP-DON-siRNA nanostructures can penetrate HeLa cells and silence gene expression at a level to commercially available lipid-based transfection reagents. Furthermore, this CPP-DON-siRNA delivery approach is biocompatible and elicits no detectable cytotoxicity while maintaining stability in serum and low $Mg^{2+}$ environments important for in vitro and in vivo human studies. The present disclosure describes the utility of DNA and RNA origami as a RNA transfection reagent and provides a basis for exploration of its application as a therapeutic reagent both in vivo and in vitro for diagnostic, treatment, and/or research purposes for cancer and other genetically-related conditions.

DESCRIPTION

Before the present methods, implementations and systems are disclosed and described, it is to be understood that this invention is not limited to specific methods, specific components, implementation, or to particular compositions, and as such may, of course, vary. It is also to be understood that the terminology used herein is for the purpose of describing particular implementations only and is not intended to be limiting. Neither are explanations that have been provided to assist in understanding the disclosure meant to be limiting.

As used in the specification and the claims, the singular forms "a," "an" and "the" include plural referents unless the context clearly dictates otherwise. Ranges may be expressed in ways including from "about" one particular value, and/or to "about" another particular value. When such a range is expressed, another implementation may include from the one particular value and/or to the other particular value. Similarly, when values are expressed as approximations, for example by use of the antecedent "about," it will be understood that the particular value forms another implementation. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. Similarly, "typical" or "typically" means that the subsequently described event or circumstance may or may not occur, and that the description includes instances where said event or circumstance occurs and instances where it does not.

Figure 1A:
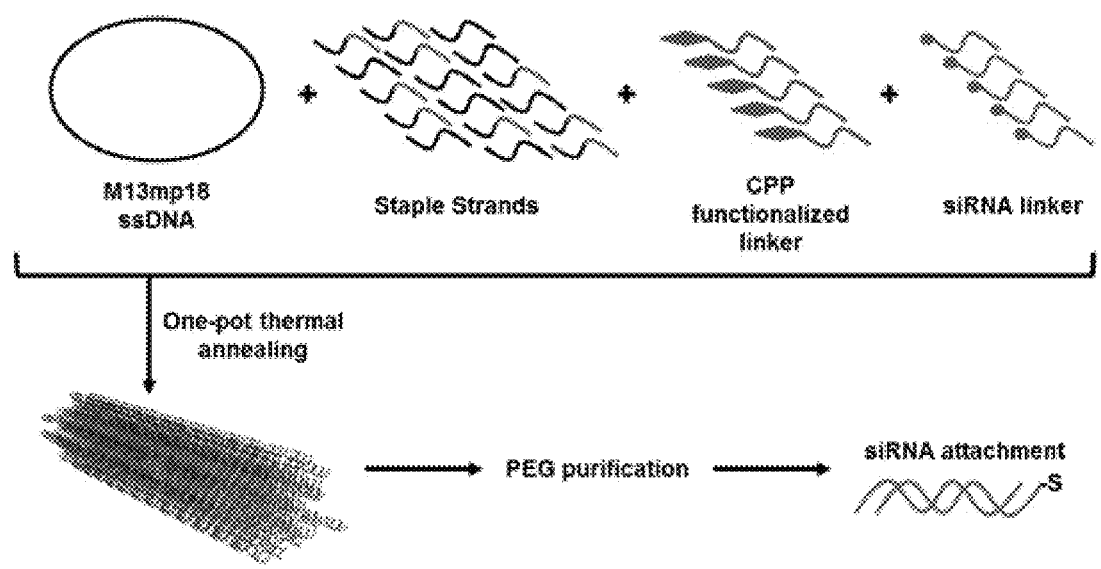
FIG. 1A shows a schematic for the thermal assembly of DNA origami nanostructures according to one aspect of the disclosed technology.

A 24 helix bundle DON to deliver siRNA molecules into human cells was created. The CPP-DON-siRNA structure of the present disclosure was designed to be approximately 100 nm by 14 nm without any functionalization using the DNA origami design software caDNAno built upon the M13mp18 (7249 nt) scaffold. By routing staples to maximize 3' termini overhanging the structure, one example design included 158 extruding single-stranded overhangs for annealing of functionalized oligonucleotides and attachment of siRNA duplexes and cell penetrating moieties. FIG. 1A shows Schematic for thermal assembly of DNA origami nanostructures from single-stranded DNA scaffold, oligonucleotide staples and functionalized oligonucleotide linkers. Reduced siRNA duplexes are incorporated following purification as described below.

Figure 1B:
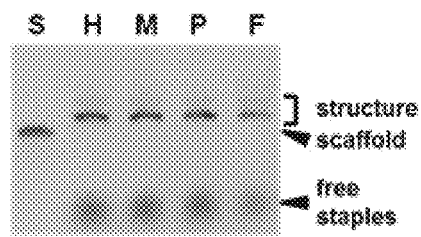
FIG. 1B shows agarose gel electrophoresis of assembled CPP containing structures.
Figure 1C:
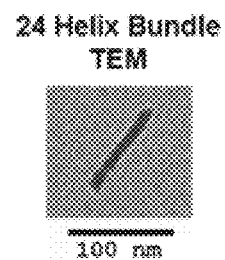
FIG. 1C shows TEM image of assembled CPP-DON with scale bar for reference.
Figure 6:
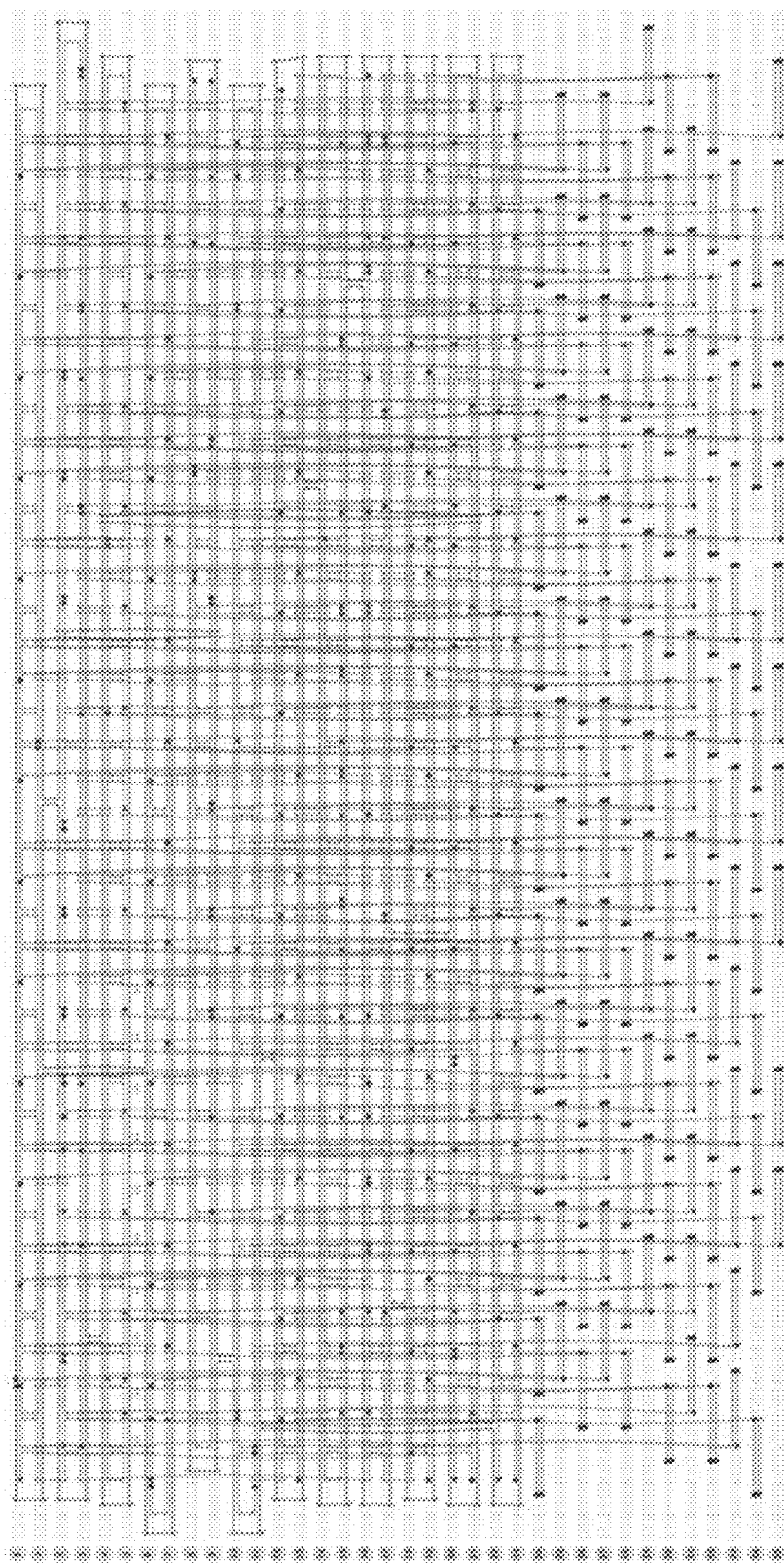
FIG. 6 shows a computer aided design of a 24 helix bundle nanostructure according to one aspect of the disclosed technology.

The complete caDNAno design schematic and oligonucleotide sequences are provided in FIG. 6 which shows a computer aided design of the 24 helix bundle nanostructure. The 24 helix bundle structure has dimensions of approximately 100 nm×14 nm without functionalization and 100 nm×18 nm after functionalization with CPP and siRNA. The design includes a total of 158 3' overhanging single strands for attachment of CPPs and siRNAs. Following a one-pot thermal annealing reaction, the assembled nanostructures were subjected to agarose gel electrophoresis to ensure complete and desired nanostructures. Agarose gel electrophoresis of assembled CPP containing structures with the identity of CPP in observed bands signified to the left are shown in FIG. 1B. Two bands were present with each of our four cell penetrating peptides corresponding to monomeric and dimeric forms of the 24 helix bundle. Excess staple oligonucleotides (included at 5× excess) are evident as faster migrating signal in the gel. Purified nanostructures were additionally visualized by transmission electron microscopy (TEM) revealing the expected 24 helix bundles. FIG. 1C shows TEM image of assembled CPP-DON with scale bar for reference.

Figure 2A:
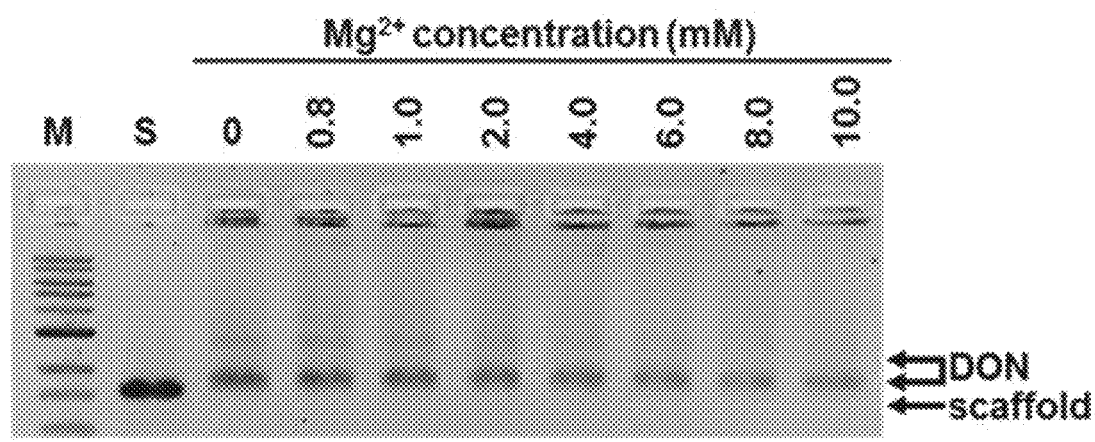
FIG. 2A shows electrophoresis of DNA origami nanostructures according to one aspect of the disclosed technology.
Figure 2B:
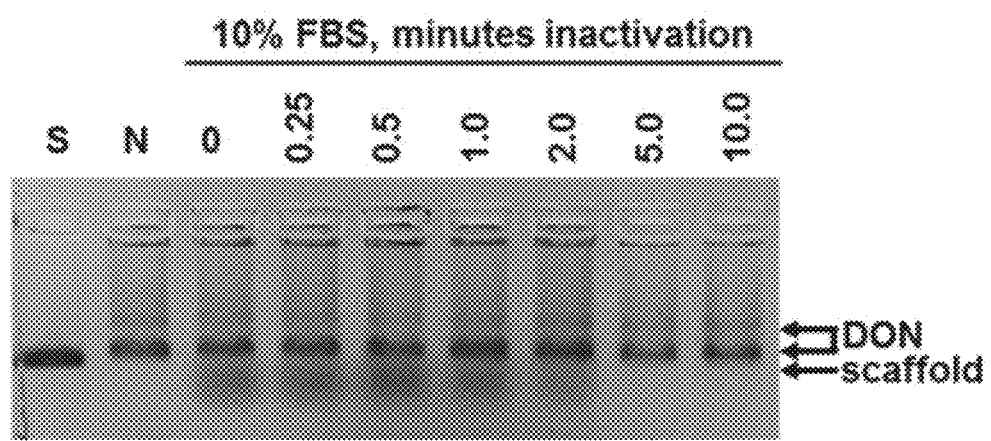
FIG. 2B shows electrophoresis of DNA origami nanostructures according to one aspect of the disclosed technology.

Successful application of the disclosed CPP-DON-siRNA nanostructure as a transfection reagent relies upon its stability in culture media. Stability was assessed under culture conditions including nuclease rich serum and weak cationic solutions. It was recently described that unmodified DNA nanostructures have varied levels of stability under conditions of Mg' depletion and in the presence of fetal bovine serum, a nuclease rich environment. To address the stability of the present CPP-DON-siRNA nanostructures in these environments, assembled nanostructures were incubated in DMEM supplemented with EDTA to chelate away existing metals or supplemented with $MgSO_4$, and also in DMEM supplemented with 10% FBS for 24 h. Even when all $Mg^{2+}$ was chelated away from the media, the disclosed CPP-DON-siRNA nanostructure remained stable (FIG. 2A). Upon incubation in DMEM medium supplemented with 10% FBS that was either untreated or heat inactivated at 75° C. for between 15 s and 10 min, the nanostructure was relatively unaffected even without heat treatment (FIG. 2B). Considering the concentration of $Mg^{2+}$ in human plasma and serum is between 0.75 mM and 1.0 mM, the disclosed assembled nanostructures will be stable in delivery applications.

Figure 3:
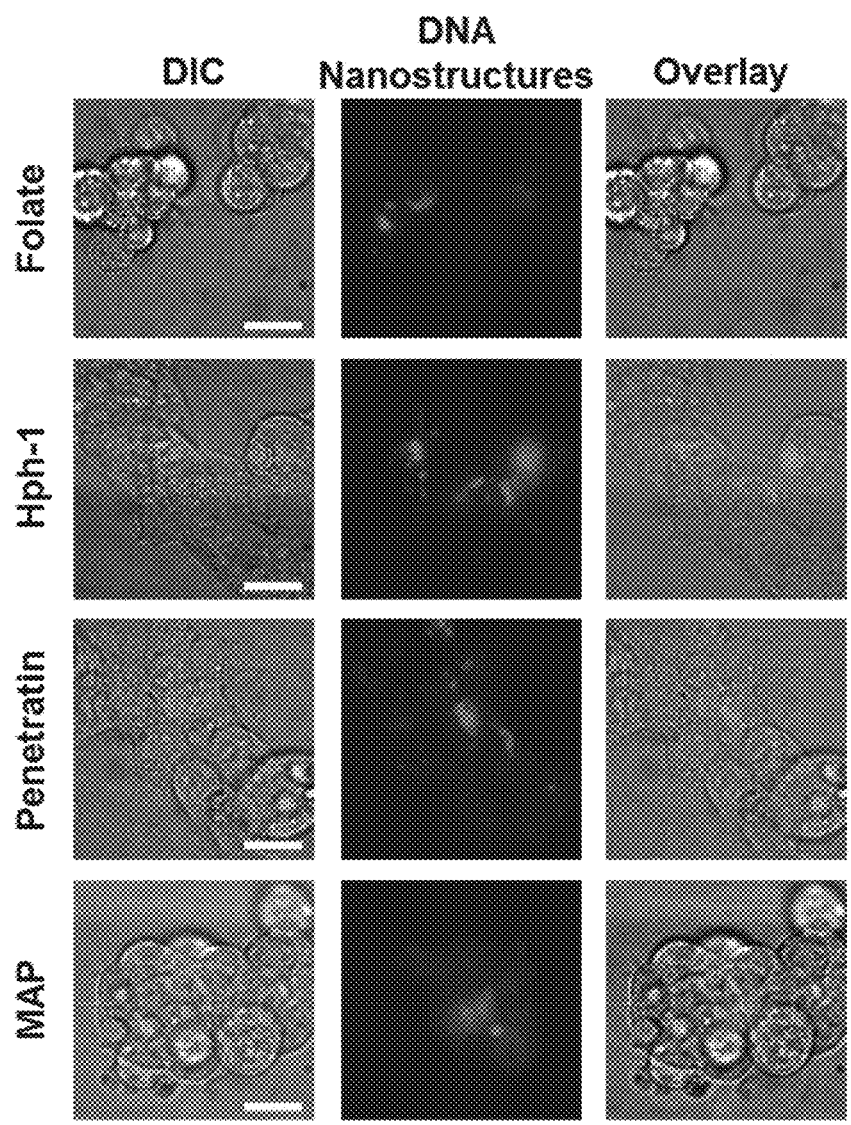
FIG. 3 shows visualization of DNA nanostructure entry into HeLa cells.
Figure 7:
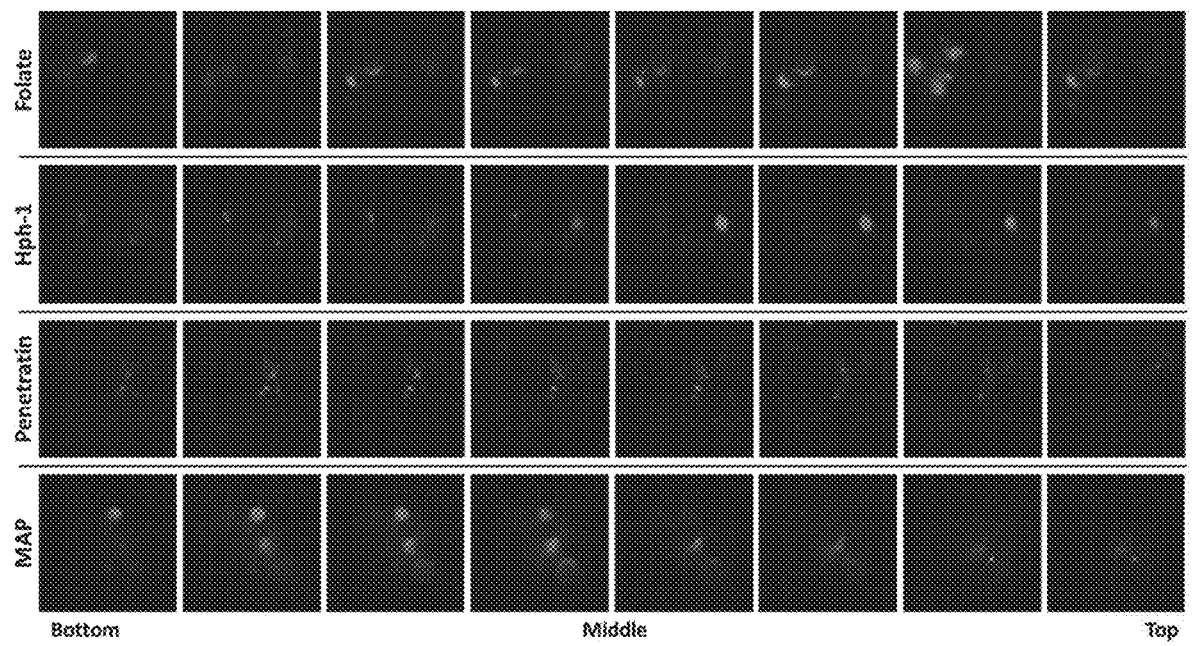
FIG. 7 shows visualization of distribution of CPP-DON-siRNA within HeLa cells.

To be used as either a transfection reagent or in disease therapy CPP-DON-siRNA nanostructures must enter cells and deliver siRNA duplexes to act in siRNA pathways. The combination of CPPs conjugated directly to siRNA duplexes or other anti-sense technologies has been well established using a range of CPPs attached to anti-sense molecules by thiol linkage for cytoplasmic release. To demonstrate the disclosed nanostructures will function as desired CPP-DON-siRNA nanostructures were incubated with HeLa cells overnight to mimic typical siRNA delivery and knockdown experiments. In order to track the entry of nanostructures and the fate of siRNAs we used siRNA duplexes labeled at the 5' end of the sense strand with Cyanine-5 (Cy5) dye which enabled detection under with 640 nm wavelength laser excitation. Using an automated Nikon TiE microscope HeLa cells were imaged by differential interference contrast (DIC) microscopy and Cy5 fluorescence. Each CPP-siRNA nanostructure was internalized by HeLa cells, with each CPP exhibiting different levels and patterns of internalized signal (FIG. 3). Since each 24 helix bundle structure possesses a 10:1 ratio of siRNA to CPP and each structure holds 158 functionalization points, the bright foci observed are expected to be the nanostructures which have not undergone complete reduction to release all siRNAs and diffuse signal intensity are presumed to be released siRNAs. To ensure signal was indeed internalized and not retained on the cell membrane, example frames were captured of a Z-series movement capturing cell images from bottom to top of cells. This demonstrated the signal is in-fact internalized and dispersed throughout the cells as shown in FIGS. 3 and 7. FIG. 3 shows a visualization of DNA nanostructure entry into HeLa cells. 24 helix bundle nanostructures containing folate or cell penetrating peptides and Cy5 labeled siRNA duplexes (640 nm excitation) were added to HeLa cells and monitored via differential interference contrast (DIC) microscopy and epifluorescence after overnight incubation.

Representative images of each CPP are shown. The left most column is DIC image of cells, the middle column depicts Cy5 labeled nanostructures or siRNA and the right most column depicts the merge of DIC and 670 nm channels. Scale bars represent 20 µm. FIG. 7 shows distribution of CPP-siRNA DONs within HeLa cells. Cy5-labelled CPP-DNA nanostructures (670 pM) were incubated overnight before epifluoresence imaging. Z-series videos were captures for each CPP-DON-siRNA nanostructure. Representative frames from the bottom to top of each series were extracted. In some examples the signal appears different for each cell penetrating moiety suggesting there are different methods and efficiencies of internalization for each peptide and folate.

Figure 4:
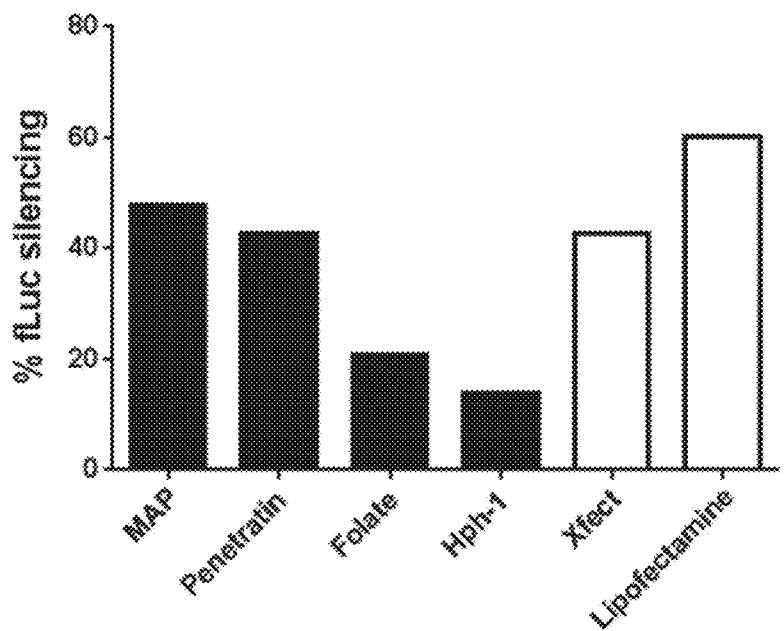
FIG. 4 is a graph showing in vitro gene silencing by CPP-DON-siRNA.

One example of in vitro gene silencing by CPP-DON-siRNA that attached with specific siRNA to fLuc mRNA for HeLa Luc-2A-GFP stable cells is presented in FIG. 4. In this example in vitro gene silencing by CPP-DON-siRNA. HeLa cells were seeded in 24 well plates and grown for 24 hours before treatment with CPP-siRNA functionalized DNA nanostructures (black bars) or commercial transfection reagents (white bars). Both treatment types used the same siRNA duplexes specific for fLuc mRNA. Quantification of fLuc and GFP signals was performed 24 hours after siRNA treatment, and measurements were normalized to the GFP signal of each sample and normalized to untreated cells (100% fLuc expression). All samples were performed in triplicate with bars representing the mean silencing. In this example as transfection reagent, CPP-DON-siRNA can achieve siRNA mediated gene silencing as effective as commercially available Lipofectamine RNAiMax (ThermoFisher Scientific) and Xfect (Clontech) transfection reagents.

Figure 5:
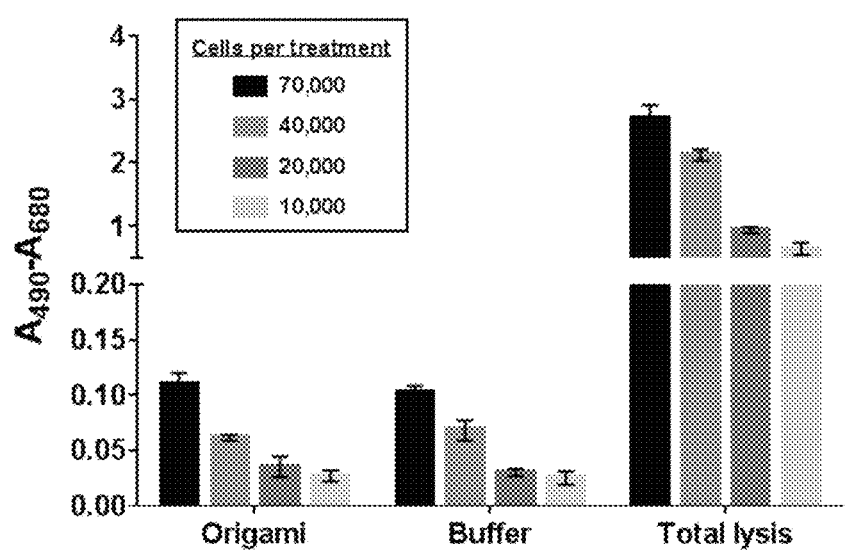
FIG. 5 is a graph showing cellular toxicity following CPP-DON-siRNA treatment.

The production of a cytotoxic response following CPP-DON-siRNA treatment was tested using a lactate dehydrogenase (LDH) assay kit (Pierce). This cytotoxicity assay measures the release of LDH into cellular media following treatment from cells which experienced membrane perturbations. Cells were treated with CPP-DON-siRNA nanostructures at 670 pM for 1 h at 37° C. before being mixed with an equal volume of reaction mixture. LDH activity was assessed by the difference between A490 and A680 measurements and total lysis controls were performed using supplied lysis buffer. No differences were observed between the CPP-DON-siRNA treatment and addition of buffer alone. As shown in FIG. 5, HeLa cells were passaged and seeded in triplicate in 24 well plates at 70,000, 40,000, 20,000 and 10,000 cells/well and grown overnight. Treatments were performed by addition of CPP-DON-siRNA (MAP as CPP) or DNA origami buffer alone. Total lysis was performed by adding lysis buffer as the treatment. Absorbance at 490 nm and 680 nm was measured and graphed as the difference for each treatment. This result correlates with previous studies on DNA origami cellular toxicity and demonstrates our CPP-DON-siRNA approach does not elicit a cytotoxic response.

The need for safe and effective methods for siRNA drug delivery, both in vitro and in vivo, led us to investigate the use of DNA origami as a cell transfection reagent. Delivery of siRNAs to numerous human cell types has been investigated using a broad array of methods including viral vectors, electroporation, and transfection reagents. Transfection reagents are widely used in research and provide advantages of high efficiency and reproducibility in many cell types, but do not perform well in primary and non-dividing cells or in vivo applications. Some of the largest hurdles for successful delivery of any RNA molecule are cell entry, RNA stability and cytotoxicity. Efficient delivery necessitates the use of a nano-carrier to transport strongly negatively charged RNA across cell membranes. Carriers such as dendrimers, polymers, lipids, gold and iron oxide nanoparticles and carbon nanotubes elicit varied toxicity and immune responses. Nanoparticle systems such as dendrimer type bio-reducible polymers (PAM-ABP), polymerized siRNA/polyethylenimine complexes, poly(oligo-D-arginine) and hydrogels have been reported as siRNA delivery vehicles and have shown varied gene silencing efficiency and cytotoxicity. A tetrahedral DNA oligonucleotide/siRNA nanoparticle with ~28.6 nm diameter was recently demonstrated to provide higher than 50% reduction in GFP expression in vitro. When applied in vivo this method showed dose-dependent accumulation of nanoparticles and tumor targeting ability while accomplishing a significant reduction of reporter gene expression in a mouse model.

The present disclosure demonstrates that a functionalized 24 helix bundle scaffolded DNA origami nanostructure of 100 nm×14 nm is capable of penetrating HeLa cell membranes, transporting siRNA cargo inside cells, and effectively silencing gene expression. Importantly, this approach elicits no cytotoxic response and is stable for at least 24 h in cell culture. The implementation of scaffolded nanostructures allows for attachment of up to 158 siRNA duplexes per structure whereas the previously reported oligonucleotide nanostructure was limited to only 6 siRNA duplexes attached to one structure. Thus, the disclosed scaffolded design provides a 26-fold improvement over current DNA nanoparticle-based siRNA approaches at an equal concentration. The present disclosure demonstrates siRNA mediated gene silencing after 24 h equivocal to commercially available Lipofectamine RNAiMax and Xfect transfection reagents using DNA origami nanostructures synthesized in a simple one-pot reaction with reducible siRNAs and widely used cell penetrating peptides or folic acid functionalized on their surface. Extension of this technique to other cell types and adjustments to the identity or density of CPPs on the nanostructure may be able to further enhance its' silencing efficacy.

The denaturation of nucleic acid nanostructures due to depletion of divalent cations and nuclease digestion in biological environments are two major challenges to successful in vitro and in vivo applications. Previous studies have reported contradictory results on the stabilities of DNA nanostructures produced via the origami method in cell culture medium. DNA origami nanostructures exposed to cell lysate were found to remain largely intact, and it has been observed that the sensitivity of nanostructures to cation depletion is design and time dependent. The present disclosure's experimental results demonstrate that the 24 helix bundle DNA origami nanostructure retains its nanostructure integrity and functions in Mg' depleted media and FBS medium (a blood product known to contain a variety of nucleases), as well as in in vitro cell culture process.

Cellular internalization of foreign materials is commonly accomplished through endocytic pathways which potentially leads to the destruction of the internalized material following fusion with nuclease rich lysosomes. Unmodified DNA origami nanostructures are known to be internalized through these same endocytic pathways which raise the risk of degradation following uptake. To accomplish effective siRNA silencing, siRNA duplexes must evade this nuclease degradation and remain in the cytoplasm to act in silencing pathways. Fortuitously, the fate of assembled DNA origami nanostructures or CPPs following internalization is not important for the effective siRNA delivery. By decorating the DNA origami nanostructures with positively charged CPPs we believe we can introduce, and perhaps favor, non-endocytic direct penetration pathways in addition to the typical endocytic pathway for uptake. At the same time, the presence of strong positively charged peptides on the surface of CPP-DON-siRNA nanostructures can assist in neutralizing the negative charges of the DNA/RNA composition and further promote migration across the cellular membrane into the cytoplasm. Hph-1 and Penetratin conjugated CPP-DON-siRNA structures yielded more internalized fluorescence than MAP conjugated structures which appear be stuck at the cell membrane (As seen in FIGS. 3 and 7). This likely reflects MAP's previously described toxicity but does not necessarily correlate with siRNA silencing as it remains possible for duplexes to dissociate into the cytoplasm while residing in the membrane. The levels of siRNA silencing observed for each cell penetrating moiety may be indicative of the dominant internalization pathway used. Folate conjugated CPP-DON-siRNA nanostructures yielded the least efficient siRNA silencing and are known to internalized through receptor mediated endocytosis which is expected to lead to lysosomal fusion and release. In one example, MAP was the most efficient CPP conjugate tested and is known to traverse cell membranes by direct penetration. While the method of internalization may be a predictor of silencing efficiency it should be noted that differences in uptake have been observed for various cell-types over an array of conjugated peptides. All together the simplicity and consistency of this origami nanostructure platform make it a promising candidate as a siRNA transfection reagent and for in vivo gene silencing or gene editing therapeutics.

Folding DNA Origami Nanostructures.

In a first example nanostructures were prepared by combining 10 nM single-stranded M13mp18 scaffold, 50 nM of each staple oligonucleotide and folding buffer (5 mM Tris pH 8, 1 mM EDTA, 12 mM $MgCl_2$). Complementary functionalized oligonucleotides were included for hybridization with overhanging staple oligos. This allowed for a one-pot assembly of CPP containing structures and provides the ability to control the ratio of CPP/siRNA by controlling the overall ratio of excess functionalized pool. In these experiments, 10 non-conjugated Amino-C6 overhang complements were included for every 1 CPP-conjugated Amino-C6 overhanging complement. One-pot assembly was carried out by rapid heat denaturation to 65° C. followed by slow cooling to 25° C. over 12 h using a thermocycler. To remove free staple oligonucleotides samples were precipitated with an equal volume of 20% (w/v) PEG 8000, 1 M NaCl, 5 mM Tris and 1 mM EDTA followed by conjugation of siRNA duplexes. Assembled structures were suspended in TE pH 8 and analyzed by electrophoresis on a 2% agarose gels (0.5×TBE, 11 mM $MgCl_2$) at 80 V for 3-4 h in an ice-water bath.

Functionalization of Oligonucleotides.

The attachment of three independent cell penetrating peptides (Table 1), folic acid and siRNA duplexes was accomplished using crosslinker chemistry to attach each to the 5' terminus of Amino-C6 modified oligonucleotides. For CPP linkages, Amino-C6 oligonucleotides were incubated in deionized water with 50× Sulfo-SMCC for 30 min at 25° C. and buffer exchanged to remove unreacted Sulfo-SMCC using buffer exchange columns. The column eluate was then mixed in a 1:1 ratio with C-terminal cysteine containing CPPs and reacted overnight at 25° C. resulting in covalently linked CPP-oligonucleotides. For coupling folic acid to linker oligonucleotides, carboxyl containing folic acid was incubated with 10× molar excess EDC and Sulfo-NHS was added at 5 mM final concentration for NHS activation. The reaction was mixed and incubated at 25° C. for 30 min before the pH was raised to pH 7.4 with 2×PBS. Equimolar Amino-C6 linker oligo was added to NHS activated folic acid and reacted overnight at 25° C. Finally, the reaction was quenched with 10 mM hydroxylamine.

siRNA Linkage to CPP-DONs.

Assembled DNA nanostructures were purified by PEG/NaCl precipitation as described above. After removal of excess staple oligonucleotides the assembled nanostructures were incubated with 0.5 mM Sulfo-LC-SPDP for 30 min at 25° C. to activate the Amino-C6 terminated oligo staples. Structures were buffer exchanged through buffer exchange columns into PBS-EDTA and 2× excess siRNA duplexes containing reduced thiol termini were added and incubated overnight at 25° C. for conjugation. The resulting linkage was: oligonucleotide-C6-S-S-siRNA duplex.

Stability of DNA Origami Nanostructures.

For cation depletion experiments DMEM medium containing 0.8 mM $Mg^{2+}$ was supplemented with 10% FBS and modified to 1 mM, 2 mM, 4 mM, 6 mM, 8 mM and 10 mM $Mg^{2+}$ by addition of $MgCl_2$ from 1 M stock solution. Each nanostructure was mixed 1:3 with adjusted media and incubated 24 h at 37° C. For serum stability experiments FBS was inactivated at 75° C. for 15 s, 30 s, 60 s, 120 s, 300 s and 600 s. DMEM was supplemented with each inactivated FBS and mixed with nanostructures in a 1:3 ratio and incubated 24 h at 37° C. Analysis of nanostructures after exposure to either cation depletion or inactivated serum was performed by agarose gel electrophoresis through a 2% agarose gel with 11 mM $MgCl_2$ and 0.5×TBE.

In Vitro Cytotoxicity Assay.

To evaluate the relative toxicity of CPP-DON-siRNA mediated delivery to cells we performed a LDH Cytotoxicity Assay. Wells containing 10,000, 20,000, 40,000 and 70,000 HeLa cells were incubated overnight at 37° C., 5% $CO_2$. The following day CPP-DON-siRNA was added at 670 pM. As controls, cells were treated with DNA origami buffer (10 mM Tris pH 8, 1 mM EDTA, 12 mM $MgCl_2$) or assay kit lysis reagent to assess spontaneous and maximum LDH activity, respectively. All assays were performed in triplicate.

Gene Silencing.

All experiments were performed using HeLa Luc-2A-GFP stable cells grown in DMEM complete medium at 37° C. with 5% $CO_2$. Cells between passage 3 and 10 were plated in 24-well tissue culture plates and incubated overnight before treatment. Lipofectamine RNAiMax and siRNA delivery systems were used as commercially available siRNA delivery comparisons following manufacturer's instructions. Assembled CPP-DON-siRNA nanostructures were added to 40,000 cells at 20 nM nanostructure concentration and 2.4 µM siRNA concentration. siRNA duplexes (sense: 5'-AUGCCAAAAACAUUAAGAAdTdT-3' (SEQ ID NO: 1), antisense: 5'-UUCUUAAUGUUUUUGG-CAUdTdT-3' (SEQ ID NO: 2)) specific to fLuc mRNA were used in silencing studies. All siRNAs were attached to Sulfo-LC-SPDP activated DONs at pyridyl disulfides using a S-SC3 terminal modified sense strand siRNA. 24 h after siRNA delivery, cells were lysed and the fLuc activity was assessed using Firefly Luciferase Glow Assay Kit. Luminescence was normalized for each cell lysate using GFP signal expressed independently of fLuc.

In the preceding examples the disclosed DNA origami nanostructures were used to deliver siRNA for illustrative purposes only. In other examples, other substances may be attached to nucleic acid nanostructures for delivery into cells. Such attached substances may include miRNA, shRNA, asRNA, mRNA, crRNA, tracrRNA and RNA vaccines.

TABLE 1

Amino acid sequence for cell penetrating peptides used in some examples. Table 1 discloses SEQ ID NOS 3-5, respectively, in order of appearance)

| Peptide | Sequence |
|---|---|
| Hph-1 | YARVRRRGPRRGGC |
| MAP | KLALKLALKALKAALKLAC |
| Penetratin | RQIKIWFQNRRMKWKKC |

Table 2. List of staple sequences used to fold the 7249 bp long M13mp18 bacteriophage scaffold into the 24 helix bundle nanostructure in some examples. The 158 staples containing overhang sequence (5'-CTCTGGT-TAACGTGTCT-3' (SEQ ID NO: 6)) for incorporation of CPP and siRNA are shown in bold.

TABLE 2

| oligo # | Sequence | |
|---|---|---|
| 24HB-1 | AAAACGAGAATTTAAAGTGCCGTTTTTAAGTAATTC | (SEQ ID NO: 7) |
| 24HB-2 | AAAAGAAATCGCCTGATAAATAAAGAATCTCTGGTTAACGTGTCT | (SEQ ID NO: 8) |
| 24HB-3 | AAAAGAGAAAATACTGAGCTACAGGCGAAAAGATTCTCTGGTTAACGTGTCT | (SEQ ID NO: 9) |
| 24HB-4 | AAAATATGCGCCGACATACT | (SEQ ID NO: 10) |
| 24HB-5 | AAACGAAGAGAAGTATATCCACCTCAAACATCAATCTCTGGTTAACGTGTCT | (SEQ ID NO: 11) |
| 24HB-6 | AAACGCATACGGTGTCTGGAAGTCAGGACTCTGGTTAACGTGTCT | (SEQ ID NO: 12) |
| 24HB-7 | AAACGTAAATTCTGGCTGTCTACCGCCATTTGTCG | (SEQ ID NO: 13) |
| 24HB-8 | AAAGCGCCCGCCAGCTCTGGTTAACGTGTCT | (SEQ ID NO: 14) |
| 24HB-9 | AAAGGTGTCCATATAAGAACGACCGTACAGTAAATGAATT | (SEQ ID NO: 15) |
| 24HB-10 | AAATTAAGGAAGTTCGTTGCGGTCCACGTAGGAATCTCTGGTTAACGTGTCT | (SEQ ID NO: 16) |
| 24HB-11 | AACATCGCCATTAAAAGGGACACAGAGACCTTCAT | (SEQ ID NO: 17) |
| 24HB-12 | AACATTTACGAGCATACCATTACTTCAAACTCTGGTTAACGTGTCT | (SEQ ID NO: 18) |
| 24HB-13 | AACCAAGTACCGCAATAGCCCGGAATAGTCCTCATTGAGGCACTCTGGT-TAACGTGTCT | (SEQ ID NO: 19) |
| 24HB-14 | AACCCATACACTGAGTTTCGTGGCTCC | (SEQ ID NO: 20) |
| 24HB-15 | AACGAGTGCTGCTCTCATTACAAGCCTT | (SEQ ID NO: 21) |
| 24HB-16 | AACGGGTTCTGTCCATCACGCCTCTGGTTAACGTGTCT | (SEQ ID NO: 22) |
| 24HB-17 | AACTGACGTATTAAACGGGGTCCTCCCTCTCTGGTTAACGTGTCT | (SEQ ID NO: 23) |
| 24HB-18 | AAGCCTGGGTGGTTGAACAACCTCTGGTTAACGTGTCT | (SEQ ID NO: 24) |
| 24HB-19 | AAGTATTTAGTTATAGCTTCTCTGGTTAACGTGTCT | (SEQ ID NO: 25) |
| 24HB-20 | AAGTGTAACAGGGCGTAATAAAAATACCCAGATGAATATGCGCGAACTG | (SEQ ID NO: 26) |
| 24HB-21 | AATAAAGAACGGATGAAAGGGAATCGCCGTTTTAG | (SEQ ID NO: 27) |
| 24HB-22 | AATAGAATATAATGCGTAGGAAGTACCACTGCTCCATGTTAC | (SEQ ID NO: 28) |
| 24HB-23 | AATCAAACAAAAAGATAACCTCGGAATAAGTAAGCCTCTGGTTAACGTGTCT | (SEQ ID NO: 29) |
| 24HB-24 | ACAAACATACATAATCATAATAAGAAACACGAGCGCTCTGGTTAACGTGTCT | (SEQ ID NO: 30) |
| 24HB-25 | ACAACTAAACAGCTTGATACCCCACGCCTCTGGTTAACGTGTCT | (SEQ ID NO: 31) |
| 24HB-26 | ACACCGCGCTCAATCGTCTGACTCGTTACTCTGGTTAACGTGTCT | (SEQ ID NO: 32) |
| 24HB-27 | ACACTAAGGAACGGCCAGCCACTAAAGCTTGGATTCTCTGGTTAACGTGTCT | (SEQ ID NO: 33) |

TABLE 2-continued

| oligo # | Sequence | |
|---|---|---|
| 24HB-28 | ACAGCTGGCATTAAAGACAGCTGCGAATTGGGCGC | (SEQ ID NO: 34) |
| 24HB-29 | ACCACATTGCGGAATCATATT | (SEQ ID NO: 35) |
| 24HB-30 | ACCACCATCAAAAATAATTCGAAAGGCTCTCTGGTTAACGTGTCT | (SEQ ID NO: 36) |
| 24HB-31 | ACCAGCGCACCATTCAATAGCAGGATTAGAACGAGGCGCAGA | (SEQ ID NO: 37) |
| 24HB-32 | ACCCCCACGATTAAACGCTCAAGCCAGCTGGAAGGCTCTGGTTAACGTGTCT | (SEQ ID NO: 38) |
| 24HB-33 | ACCGTTCATGTGTATACCAAATAAGAAACCCAAAACTCTGGTTAACGTGTCT | (SEQ ID NO: 39) |
| 24HB-34 | ACGAGGCGGGGTAATAGTAAAACAGTTCTCTGGTTAACGTGTCT | (SEQ ID NO: 40) |
| 24HB-35 | ACGTTGTAGCTGGCTCGCCTGAATTACCCTCTGGTTAACGTGTCT | (SEQ ID NO: 41) |
| 24HB-36 | ACTATCATGCAAAACATTTTCCTACTAAAGGCAAGGCAAAGA | (SEQ ID NO: 42) |
| 24HB-37 | AGAGCAATTCAACGCAGTTGGGTTATAT | (SEQ ID NO: 43) |
| 24HB-38 | AGATAGCAGCTAAATCGGTTGGGTAAAGCTCTGGTTAACGTGTCT | (SEQ ID NO: 44) |
| 24HB-39 | AGATGATGGCAATTTATCAAACTCTGGTTAACGTGTCT | (SEQ ID NO: 45) |
| 24HB-40 | AGATTAACAATCATTTAATATTGATTGTATCACCTCTGGTTAACGTGTCT | (SEQ ID NO: 46) |
| 24HB-41 | AGCATGTGACGCTGTTTTTCACCTGAACCACAATCCTCTGGTTAACGTGTCT | (SEQ ID NO: 47) |
| 24HB-42 | AGCCCCCGAATAAGACGAGAATACGTGA | (SEQ ID NO: 48) |
| 24HB-43 | AGCGGGCCTTTGACGATTCACCAGAAGAGTAGATTCTCTGGTTAACGTGTCT | (SEQ ID NO: 49) |
| 24HB-44 | AGGAATTTAGTAATTTTCAACAGACGTTTCAGGAG | (SEQ ID NO: 50) |
| 24HB-45 | AGGAGGCGCGATTATACCAAACTCTGGTTAACGTGTCT | (SEQ ID NO: 51) |
| 24HB-46 | AGGGCGAGCACTAAGTACAGAGCCAGGGCTGCAAGGCGATTAAGGACCTGAAAGCG | (SEQ ID NO: 52) |
| 24HB-47 | AGGGCTTACCGGAAATCAATACTCTGGTTAACGTGTCT | (SEQ ID NO: 53) |
| 24HB-48 | AGGGTAGATATATTTTTCTTAATAGATTATTAATCTCTGGTTAACGTGTCT | (SEQ ID NO: 54) |
| 24HB-49 | AGGTGAACGGTCGCCTCTGGTTAACGTGTCT | (SEQ ID NO: 55) |
| 24HB-50 | AGTAAATTCTATCACTCTGGTTAACGTGTCT | (SEQ ID NO: 56) |
| 24HB-51 | AGTAGATTCGCAGTATGAAATACTCTGGTTAACGTGTCT | (SEQ ID NO: 57) |
| 24HB-52 | ATAAAGCAAAAGCCTTTAATGCTCTGGTTAACGTGTCT | (SEQ ID NO: 58) |
| 24HB-53 | ATAACATGTTTGAAGGCAGAGTCGGTGCCTTGCATGCCTGCA | (SEQ ID NO: 59) |
| 24HB-54 | ATAACCGCAACGGCGCCAGCTATTGCCCAGGAATTCTCTGGTTAACGTGTCT | (SEQ ID NO: 60) |
| 24HB-55 | ATAATCCTTTGTTAGGCAAAGAAGGTAA | (SEQ ID NO: 61) |
| 24HB-56 | ATACTTCTTAAATTCAGGCTGGAGAATATA | (SEQ ID NO: 62) |
| 24HB-57 | ATAGCAGATAAATAACAACGCTTACGCCAAAACGACGGCCAG | (SEQ ID NO: 63) |
| 24HB-58 | ATCAATTAGGGATAACAAACTAGAGGCGCTCAGCACTCTGGTTAACGTGTCT | (SEQ ID NO: 64) |
| 24HB-59 | ATCAGGTCCTCCGGCTTAGAGCTCTGGTTAACGTGTCT | (SEQ ID NO: 65) |
| 24HB-60 | ATCATCATTTTAACCTCCAGCGTTCAGC | (SEQ ID NO: 66) |
| 24HB-61 | ATCATGGAAACCAAAATTCGTAAAACTCTCTGGTTAACGTGTCT | (SEQ ID NO: 67) |
| 24HB-62 | ATCATTTCCTTCCTGTTTGAGAGTCCTGATAATCGCGAACG | (SEQ ID NO: 68) |
| 24HB-63 | ATCGTAACCGTGCAACAACTAAAGGAATCCTCATAGAACCGC | (SEQ ID NO: 69) |
| 24HB-64 | ATGAAACCATCGAATTAGAGCCAGCTAGAAGGAGACTCCTCATAAG | (SEQ ID NO: 70) |
| 24HB-65 | ATGAACGGTAATCGCATTAAATTTTGTCGCTTCT | (SEQ ID NO: 71) |
| 24HB-66 | ATGCCGGTTTAAATGTAATACTTTTGCGAAAATAA | (SEQ ID NO: 72) |

TABLE 2-continued

| oligo # | Sequence | |
|---|---|---|
| 24HB-67 | ATGGTCAATTAAGACTCTGGTTAACGTGTCT | (SEQ ID NO: 73) |
| 24HB-68 | ATGGTTGGCTAGGGCCGTAAAAAAACCGTGGGCTTCTCTGGTTAACGTGTCT | (SEQ ID NO: 74) |
| 24HB-69 | ATTAATTTTCCCTTTTTAATGAAAAACACAAAAGGCTCTGGTTAACGTGTCT | (SEQ ID NO: 75) |
| 24HB-70 | ATTATACTACAGGAAAGGATTAAGCAAACGAGCCAGTAATAA | (SEQ ID NO: 76) |
| 24HB-71 | ATTATTAAGAATGGTATAAGTCTCATCGACAATAAA | (SEQ ID NO: 77) |
| 24HB-72 | ATTATTTTGAATACTTCGCTACAACATG | (SEQ ID NO: 78) |
| 24HB-73 | ATTCAAACAATATGATTCTCCACTCGTAATTTGAGCTCTGGTTAACGTGTCT | (SEQ ID NO: 79) |
| 24HB-74 | ATTGAGTAACTATAGAACGCGTCAGGAAAAACAACAACATCA | (SEQ ID NO: 80) |
| 24HB-75 | ATTGCATAATCAGGAGGCTTTTAACCCTGTTTTTCCTCTGGTTAACGTGTCT | (SEQ ID NO: 81) |
| 24HB-76 | CAAATCACCATAGGGTGAAGCATAACGAACAAAAACGCAATAATAAGTTTAGC | (SEQ ID NO: 82) |
| 24HB-77 | CAACAGTTGCGGGATACCAACTTTAGCGT | (SEQ ID NO: 83) |
| 24HB-78 | CAACATCAGCTTTCCGGCACTAAATCAAGAATCGCTCTGGTTAACGTGTCT | (SEQ ID NO: 84) |
| 24HB-79 | CAACTTTCCCGATTCGAGAAACTCTGGTTAACGTGTCT | (SEQ ID NO: 85) |
| 24HB-80 | CACAAACTGAGATTCTGGTTTCTCTGGTTAACGTGTCT | (SEQ ID NO: 86) |
| 24HB-81 | CACCACCAATCAGTTCACCGAGGTAAATAATGAAACTCTGGTTAACGTGTCT | (SEQ ID NO: 87) |
| 24HB-82 | CACCACCGATAAGATCAACATATTTTGTAAAGTCACTCTGGTTAACGTGTCT | (SEQ ID NO: 88) |
| 24HB-83 | CACCCTCAGAGCCAATTCCACTGAATCGCGGAACGCTCTGGTTAACGTGTCT | (SEQ ID NO: 89) |
| 24HB-84 | CACTACGTGAGGCCAAACTATTCAATATGATTATCCTCTGGTTAACGTGTCT | (SEQ ID NO: 90) |
| 24HB-85 | CAGAAAACGAAAGAGATACATCATGATTACCGAAGCTCTGGTTAACGTGTCT | (SEQ ID NO: 91) |
| 24HB-86 | CAGACGAACCAAAACAATAGG | (SEQ ID NO: 92) |
| 24HB-87 | CAGACTCATCTTTTCATAATCAAAATCGTTTGCC | (SEQ ID NO: 93) |
| 24HB-88 | CAGAGCCGCCACCCGGTAATATTAAGAACAGTTTGCTCTGGTTAACGTGTCT | (SEQ ID NO: 94) |
| 24HB-89 | CAGCCATTATCATAAAATTCTACGTGGCACAGACAGAATGGC | (SEQ ID NO: 95) |
| 24HB-90 | CAGTTACCACCCAGGATTAGTCAAGAACCAAGAGTCCAAATCCGCTGCG | (SEQ ID NO: 96) |
| 24HB-91 | CATATATAGAGGGTGCTTTCAGTTTGAGAGCACTACTCTGGTTAACGTGTCT | (SEQ ID NO: 97) |
| 24HB-92 | CATCAGTAAATAAAGTGTATCGGTATTA | (SEQ ID NO: 98) |
| 24HB-93 | CATTGACGTACCTTACTAAAGAAGACACGCTAATACTCTGGTTAACGTGTCT | (SEQ ID NO: 99) |
| 24HB-94 | CCAATCAAACAAGAGGAGAAGGAACCCTCTCTGGTTAACGTGTCT | (SEQ ID NO: 100) |
| 24HB-95 | CCACCAGCAGTCACACGACCAGCGTACTCTCTGGTTAACGTGTCT | (SEQ ID NO: 101) |
| 24HB-96 | CCACCCTGAAGTTTGACCATACTCTGGTTAACGTGTCT | (SEQ ID NO: 102) |
| 24HB-97 | CCCAAAAACTCGCGCAGAGGCCTCTGGTTAACGTGTCT | (SEQ ID NO: 103) |
| 24HB-98 | CCCTCAACGGCCTTCTGTTTCCACAACAGGGTTGA | (SEQ ID NO: 104) |
| 24HB-99 | CCCTTTTAACATTACCAATAAGTGTAGAAATAATT | (SEQ ID NO: 105) |
| 24HB-100 | CCGGTTGCATAGCGAATTTCAACGGGAGATGGTTTCTCTGGTTAACGTGTCT | (SEQ ID NO: 106) |
| 24HB-101 | CCTCAAATTTTAATTCGAGCTCTCTGGTTAACGTGTCT | (SEQ ID NO: 107) |
| 24HB-102 | CCTCAGAATGGCTTAGAGCCACTCTGGTTAACGTGTCT | (SEQ ID NO: 108) |
| 24HB-103 | CCTGACTCAGAAGCTCATTTGACCGAGGAGTTACCCTCTGGTTAACGTGTCT | (SEQ ID NO: 109) |
| 24HB-104 | CCTGGCCGGGAAACCTGTCGTTACAGAGCTCTGGTTAACGTGTCT | (SEQ ID NO: 110) |
| 24HB-105 | CCTTTAAAGTATTCAAACAACTCTGGTTAACGTGTCT | (SEQ ID NO: 111) |

TABLE 2-continued

| oligo # | Sequence | |
|---|---|---|
| 24HB-106 | CGAACCTTCGGAACGAACGGTATCGGAACGAAAGGCTCTGGTTAACGTGTCT | (SEQ ID NO: 112) |
| 24HB-107 | CGACGGCGGATCCGTTCCCCAGAACCTCTGGTTAACGTGTCT | (SEQ ID NO: 113) |
| 24HB-108 | CGCAACTTCTAGAGAGGAAAAAGGGATTCTCTGGTTAACGTGTCT | (SEQ ID NO: 114) |
| 24HB-109 | CGCCACCGGCCGGACCAGTAGCCAAAGAGGGAAGCCTCTGGTTAACGTGTCT | (SEQ ID NO: 115) |
| 24HB-110 | CGCTGAGTGGAAATACCTACAGCTAAACCTCTGGTTAACGTGTCT | (SEQ ID NO: 116) |
| 24HB-111 | CGGATATATTCAGTTTATTAGCTCTGGTTAACGTGTCT | (SEQ ID NO: 117) |
| 24HB-112 | CGGCAAAATCCCTTCGTTAATCTCTGGTTAACGTGTCT | (SEQ ID NO: 118) |
| 24HB-113 | CGGTCAATCAAGAGGTGTACTTCAGAACCTCTGGTTAACGTGTCT | (SEQ ID NO: 119) |
| 24HB-114 | CGTAACCCGCCGCGCTTAATGCGCCGCT | (SEQ ID NO: 120) |
| 24HB-115 | CGTTTGCGTAGCGCTTTATCCAGAGCCTATCCCAACTCTGGTTAACGTGTCT | (SEQ ID NO: 121) |
| 24HB-116 | CTATTATACAGTGCCCAGAGCCTCTGGTTAACGTGTCT | (SEQ ID NO: 122) |
| 24HB-117 | CTGAGTATAGCTGAGAGCGAGCGAACGTAGAGCCGCTCTGGTTAACGTGTCT | (SEQ ID NO: 123) |
| 24HB-118 | CTGGAGCTCTGAGAGCTGATGGATAACCATAAAAGCTCTGGTTAACGTGTCT | (SEQ ID NO: 124) |
| 24HB-119 | CTTATCCTAATTTAATACCGAGCTATTACTCTGGTTAACGTGTCT | (SEQ ID NO: 125) |
| 24HB-120 | CTTATTATAGTTTGGTAGAAAACCCTCAGTTAGCG | (SEQ ID NO: 126) |
| 24HB-121 | CTTGCCTAATCAACCGGAATTCTCTGGTTAACGTGTCT | (SEQ ID NO: 127) |
| 24HB-122 | CTTTAATACAGTAAAACAAAACTCTGGTTAACGTGTCT | (SEQ ID NO: 128) |
| 24HB-123 | CTTTGCCTAACAACCACGTTGATCATACTAGTAGT | (SEQ ID NO: 129) |
| 24HB-124 | GAAAAATTTGCAACGATCCCC | (SEQ ID NO: 130) |
| 24HB-125 | GAAACAGTCAAGAACAGTACCTTAACGTGAACGAACTCTGGTTAACGTGTCT | (SEQ ID NO: 131) |
| 24HB-126 | GAAATTATTCATTAGATTTTTCTCTGGTTAACGTGTCT | (SEQ ID NO: 132) |
| 24HB-127 | GAACAAGTGACGGGGAAGCGCGAAACAAGTTGTTCCTGGCTCCTCTGGT-TAACGTGTCT | (SEQ ID NO: 133) |
| 24HB-128 | GAACGTGGGGAGCCGAAAGAG | (SEQ ID NO: 134) |
| 24HB-129 | GAACTGGTTCGCAAAGCATT | (SEQ ID NO: 135) |
| 24HB-130 | GAATCAAACCGGAACCGTATATTTAATTACGTCAACTCTGGTTAACGTGTCT | (SEQ ID NO: 136) |
| 24HB-131 | GAATCAGAACGTGGTAGAGCTAGTCCACTACCTTACTCTGGTTAACGTGTCT | (SEQ ID NO: 137) |
| 24HB-132 | GAATCCTAGAGGCATGTGTCGAAGCATAAAGTGTA | (SEQ ID NO: 138) |
| 24HB-133 | GAATTATAATCGTCCCGTGTGCCTTTACATTGAGGCTCTGGTTAACGTGTCT | (SEQ ID NO: 139) |
| 24HB-134 | GACAACAGGACTAATCCAGTCCTGAGAGATGCAGACTCTGGTTAACGTGTCT | (SEQ ID NO: 140) |
| 24HB-135 | GACGACGAGAACAAGCAAGCCGTCGAGATACGAGCCGGAAATCCG | (SEQ ID NO: 141) |
| 24HB-136 | GAGAATACTAAAGTCCCTCAGATAGCGTGAATCCCCTCTGGTTAACGTGTCT | (SEQ ID NO: 142) |
| 24HB-137 | GAGATGGAACAGTTAATGCCGTAACAAA | (SEQ ID NO: 143) |
| 24HB-138 | GAGGGAACTTGAGCTAAGAAC | (SEQ ID NO: 144) |
| 24HB-139 | GAGGGTAGAACGCGAGAAAACAGAAGAGCTCTGGTTAACGTGTCT | (SEQ ID NO: 145) |
| 24HB-140 | GAGGTGATATTTCACATTGGCAGAGCACGCTCTGGTTAACGTGTCT | (SEQ ID NO: 146) |
| 24HB-141 | GATAAAAGATCTACCGTCTGGTGCGGAAGTTATCTCTGGTTAACGTGTCT | (SEQ ID NO: 147) |
| 24HB-142 | GATAGGTCCGTCGGATATTCACTCTGGTTAACGTGTCT | (SEQ ID NO: 148) |
| 24HB-143 | GATTCCCGAAAATAAATAATACTCTGGTTAACGTGTCT | (SEQ ID NO: 149) |

TABLE 2-continued

| oligo # | Sequence | |
|---|---|---|
| 24HB-144 | GATTTAGATTGTATAAAAAAACACCAGTGCAAGCCTAGCGAGTCTTTAC | (SEQ ID NO: 150) |
| 24HB-145 | GCAAACTCGATTGGCCTTGGTCATAAATGAACCAG | (SEQ ID NO: 151) |
| 24HB-146 | GCAAGCGCTCACTGCCCGCTTAGACTTTCTCTGGTTAACGTGTCT | (SEQ ID NO: 152) |
| 24HB-147 | GCAATAGCTATCTTAAGACTCCTCTGGTTAACGTGTCT | (SEQ ID NO: 153) |
| 24HB-148 | GCACCGTGGAACCGCAGTGCCTTGAGTATCTGAAACATGAAA | (SEQ ID NO: 154) |
| 24HB-149 | GCATTAGTCTTCTGACCTAAAAGAATCCCTCTGGTTAACGTGTCT | (SEQ ID NO: 155) |
| 24HB-150 | GCCCCAGACTCACATTAATTGTCCATTACTCTGGTTAACGTGTCT | (SEQ ID NO: 156) |
| 24HB-151 | GCCGGCGAGCGGGATTTTGACCTGCAACTATCAAACTCTGGTTAACGTGTCT | (SEQ ID NO: 157) |
| 24HB-152 | GCGAAAGTGCAGGGTCAGCTTATAATACTTAAATCCTCTGGTTAACGTGTCT | (SEQ ID NO: 158) |
| 24HB-153 | GCGACATTCAACCGAGAGAGACTCTGGTTAACGTGTCT | (SEQ ID NO: 159) |
| 24HB-154 | GCGAGGCATATTTAAGGCGTTACCTTGCCTCTGGTTAACGTGTCT | (SEQ ID NO: 160) |
| 24HB-155 | GCGGTCAAAGTTTTGGCCCACACACCAGCTCTGGTTAACGTGTCT | (SEQ ID NO: 161) |
| 24HB-156 | GCTAAAGGTGAATTATCACCGAGCGACACTCTGGTTAACGTGTCT | (SEQ ID NO: 162) |
| 24HB-157 | GCTGAAAAAATTAAGCCTCAGGAAAGGCCTCTGGTTAACGTGTCT | (SEQ ID NO: 163) |
| 24HB-158 | GCTTTGAACCATCGGATAGTTCTTTAGGTAACATTCTGGTTAACGTGTCT | (SEQ ID NO: 164) |
| 24HB-159 | GGAACCGTGCCAAGGGGCCTCCAAGTTACAAAAAGGAAGATTAGGGCGAGCATTTT | (SEQ ID NO: 165) |
| 24HB-160 | GGAAGAAGTCATACTTTGCTCATCATTACCGCGCCACTTAA | (SEQ ID NO: 166) |
| 24HB-161 | GGAAGCCCGAGAATTGCCAGAATAGTAAACGGGCACTCTGGTTAACGTGTCT | (SEQ ID NO: 167) |
| 24HB-162 | GGAAGGGTGCTTTCAATGGATGCGGTCAAACAGACTCTGGTTAACGTGTCT | (SEQ ID NO: 168) |
| 24HB-163 | GGCCGCTCGTCACCGTTTGCGCAGGGTGCGTTTAC | (SEQ ID NO: 169) |
| 24HB-164 | GGGCGATTTGGGGTTGGCTGATAGAACCCTTCTTTGGGTAACCCAGGCGCA | (SEQ ID NO: 170) |
| 24HB-165 | GGGTACCCGCCATTGTAAACGATGTACCCTCTGGTTAACGTGTCT | (SEQ ID NO: 171) |
| 24HB-166 | GGTATTCCATTTGGGATAGCACTCTGGTTAACGTGTCT | (SEQ ID NO: 172) |
| 24HB-167 | GGTCAGACCAACAGGTTTCATGCAACATCACAAGACTCTGGTTAACGTGTCT | (SEQ ID NO: 173) |
| 24HB-168 | GGTCGACGTTGGGAGTATAAGGAAAAGCCTCTGGTTAACGTGTCT | (SEQ ID NO: 174) |
| 24HB-169 | GTAATGGATCTCCACGGTTTAAGTTAAACTCTGGTTAACGTGTCT | (SEQ ID NO: 175) |
| 24HB-170 | GTTAGAACCTACCAAGTGCCACTCTGGTTAACGTGTCT | (SEQ ID NO: 176) |
| 24HB-171 | GTTGAGTAGTACAACGGAGATATCTTTGCTCTGGTTAACGTGTCT | (SEQ ID NO: 177) |
| 24HB-172 | GTTGGCAGAGTAGAAGAACTCACCGAGTCTCTGGTTAACGTGTCT | (SEQ ID NO: 178) |
| 24HB-173 | GTTTAGTTTCCTTAATCAACAATAGATAGGGACGAGCGGAGT | (SEQ ID NO: 179) |
| 24HB-174 | GTTTGATGGGTGCCAATTCCACTGTGTGAAATTGTTATGGGATT | (SEQ ID NO: 180) |
| 24HB-175 | TAACGATGAAAGGATCTGCCAGTAGCCAAGCTATTCTCTGGTTAACGTGTCT | (SEQ ID NO: 181) |
| 24HB-176 | TAAGAATTACCAGTAAATCAACTACAATGTTTTCATCGGCAT | (SEQ ID NO: 182) |
| 24HB-177 | TAAGCCCCATACATCTCTGGTTAACGTGTCT | (SEQ ID NO: 183) |
| 24HB-178 | TAAGTTTGTTTTAAATATGCATAATTGCCTCTGGTTAACGTGTCT | (SEQ ID NO: 184) |
| 24HB-179 | TAATCAGAAGGCACCAACCTACTCTGGTTAACGTGTCT | (SEQ ID NO: 185) |
| 24HB-180 | TAATCATTGTGAATTATTAAACTCTGGTTAACGTGTCT | (SEQ ID NO: 186) |
| 24HB-181 | TAATGCATGTAAATGACTACCCTCTGGTTAACGTGTCT | (SEQ ID NO: 187) |
| 24HB-182 | TACATAACGCCAAATTCACCGCTCTGGTTAACGTGTCT | (SEQ ID NO: 188) |

TABLE 2-continued

| oligo # | Sequence | |
|---|---|---|
| 24HB-183 | TAGGCCGAGGTGCGCTGGCCTCTGGTTAACGTGTCT | (SEQ ID NO: 189) |
| 24HB-184 | TATAACGAAGAAAGCCCTAAAGACTCCATCAACTTCTCTGGTTAACGTGTCT | (SEQ ID NO: 190) |
| 24HB-185 | TATATTTAAAGCGGCTCTGGTTAACGTGTCT | (SEQ ID NO: 191) |
| 24HB-186 | TATCCCATCCTAATTGACCCTGCAATGCCTCTGGTTAACGTGTCT | (SEQ ID NO: 192) |
| 24HB-187 | TATCGCGTGCTTTAAATGTTTAGACTGGAACCGCC | (SEQ ID NO: 193) |
| 24HB-188 | TATGTGAAAGAAGAAAACAATAAATTGCTAAAACACTCTGGTTAACGTGTCT | (SEQ ID NO: 194) |
| 24HB-189 | TCAAAGCATTCATTCCAATACTCAACTAAGTTGCACTCTGGTTAACGTGTCT | (SEQ ID NO: 195) |
| 24HB-190 | TCAATAGGCTTTCGTTTTCACCTGTAGC | (SEQ ID NO: 196) |
| 24HB-191 | TCAATAGTGAATTTAGACAAAATTGAGCCACGGAACTCTGGTTAACGTGTCT | (SEQ ID NO: 197) |
| 24HB-192 | TCAGAGACAAATCCAATCGCAATCAAAACTCTGGTTAACGTGTCT | (SEQ ID NO: 198) |
| 24HB-193 | TCAGATAAAAATCAAACGTCACCA | (SEQ ID NO: 199) |
| 24HB-194 | TCATAGGAAACAAGGCTCATTTATTCCTCTGGTCACTCTGGTTAACGTGTCT | (SEQ ID NO: 200) |
| 24HB-195 | TCATTCCAACAGTTACCGGAACTCTGGTTAACGTGTCT | (SEQ ID NO: 201) |
| 24HB-196 | TCCAAATTACTAGACAACGCT | (SEQ ID NO: 202) |
| 24HB-197 | TCCTTTTAGAGCCGAGTCTCTACTAACGCCGAAATCTCTGGTTAACGTGTCT | (SEQ ID NO: 203) |
| 24HB-198 | TCTTTCCAGTTTCACGACAGTATCGGCCCCTGTTT | (SEQ ID NO: 204) |
| 24HB-199 | TCTTTCCTGAATCTGGTTTTGCCAAATCAACCCCTGCCTATTCCCGACT | (SEQ ID NO: 205) |
| 24HB-200 | TCTTTGATGAGGAAGCAAAGAACTCTGGTTAACGTGTCT | (SEQ ID NO: 206) |
| 24HB-201 | TGAACACAATATATCCGACAACGCCATTGAGCTCGAATTCGTA | (SEQ ID NO: 207) |
| 24HB-202 | TGAGCAAGTGAATAAAATAAGCGTCAAAATTGACGCTCTGGTTAACGTGTCT | (SEQ ID NO: 208) |
| 24HB-203 | TGAGGCTACAGCATGCCAACGCAGTGAGGAGCAACCTCTGGTTAACGTGTCT | (SEQ ID NO: 209) |
| 24HB-204 | TGCGATTAGTTTTAGAGGCTG | (SEQ ID NO: 210) |
| 24HB-205 | TGCTGAAGAACAATATTACCGTACGCCACTCTGGTTAACGTGTCT | (SEQ ID NO: 211) |
| 24HB-206 | TGTCCAGGTGCCGGTCATAGGCTGGTAGTTTTTACTCTGGTTAACGTGTCT | (SEQ ID NO: 212) |
| 24HB-207 | TGTTTAAAATAAACAATTGAGGGATGTGTTTTCCCAGTCACGGACAGAT | (SEQ ID NO: 213) |
| 24HB-208 | TTAATTATACCTTTTGTTTAGATTATTTAATTTGCCTCTGGTTAACGTGTCT | (SEQ ID NO: 214) |
| 24HB-209 | TTAGACAAACACTCTTGTATCTAGCCCGGACGTTGCTCTGGTTAACGTGTCT | (SEQ ID NO: 215) |
| 24HB-210 | TTAGAGAAGGAGGTTAAAGCCCAGGTAGAAATCCTCTGGTTAACGTGTCT | (SEQ ID NO: 216) |
| 24HB-211 | TTAGCAACTCAGAGTTGATGACAGTCAGAGATAGGCTCTGGTTAACGTGTCT | (SEQ ID NO: 217) |
| 24HB-212 | TTAGCCGGCGGGGTATGGCTTCCACCACCTCTGGTTAACGTGTCT | (SEQ ID NO: 218) |
| 24HB-213 | TTCAGGTTTTTACATCGGGAGTGATGAACTCTGGTTAACGTGTCT | (SEQ ID NO: 219) |
| 24HB-214 | TTCATGACCGTTGTAGCAAATCTCTGGTTAACGTGTCT | (SEQ ID NO: 220) |
| 24HB-215 | TTCGACAGTGGGAAATTGACCATTAGCAAGGTGGC | (SEQ ID NO: 221) |
| 24HB-216 | TTCTGTATCATTTCATTGCTTGCACGTAAGTATTACTCTGGTTAACGTGTCT | (SEQ ID NO: 222) |
| 24HB-217 | TTCTGTATCCGCTCACTAATGAGGTAATGCCTCTGGTTAACGTGTCT | (SEQ ID NO: 223) |
| 24HB-218 | TTGAAAAATAATCACAAATATTGAATAAAGCAAATCTCTGGTTAACGTGTCT | (SEQ ID NO: 224) |
| 24HB-219 | TTGCTGAAAATTCATAATTAACCTCTGGTTAACGTGTCT | (SEQ ID NO: 225) |
| 24HB-220 | TTGCTGATCGCACAATAGGTGAGAGTCTCTGGTTAACGTGTCT | (SEQ ID NO: 226) |
| 24HB-221 | TTTAAAAATCAACATTAAATGTTAAATTACTCTGGTTAACGTGTCT | (SEQ ID NO: 227) |

TABLE 2-continued

| oligo # | Sequence | |
|---|---|---|
| 24HB-222 | TTTGAATCATTTAATATTAGT | (SEQ ID NO: 228) |
| 24HB-223 | TTTGAGAATTTTTACCTTTATGAAACAATGTTAGCCTCTGGTTAACGTGTCT | (SEQ ID NO: 229) |
| 24HB-224 | TTTGCGGGCCGCCAAGTAAGCAAATCTAATAAATCCTCTGGTTAACGTGTCT | (SEQ ID NO: 230) |
| 24HB-225 | TTTTCACCGCGGGGACAACGCGTTGAAA | (SEQ ID NO: 231) |
| 24HB-226 | TTTTCATCTGTAGCGGTCATTCTCTGGTTAACGTGTCT | (SEQ ID NO: 232) |
| 24HB-227 | TTTTTAACATTGCCAACGCCAGAAGGAGAGTTGAACTCTGGTTAACGTGTCT | (SEQ ID NO: 233) |

While the disclosure has been illustrated and described in detail in the figures and foregoing description, the same is to be considered as illustrative and not restrictive in character, it being understood that only selected embodiments have been shown and described, and that all changes, modifications and equivalents that come within the spirit of the disclosures described heretofore and/or defined by the following claims are desired to be protected, including any variations, uses, or adaptations that follow the general principles herein, and such departures as come within known or customary practice within the art to which the present disclosure pertains. In addition, all publications cited herein are indicative of the level of skill in the art, and are hereby incorporated by reference in their entirety as if each had been individually incorporated by reference and fully set forth.

What is claimed is:

1. A nucleic acid nanostructure, comprising:
a DNA or RNA scaffold;
at least one single stranded nucleic acid staple strand complementary to the scaffold;
at least one cell penetrating peptide attached to the at least one staple strand; and
at least one therapeutic substance attached to the at least one staple strand;
wherein the at least one cell penetrating peptide is positively charged;

wherein the nanostructure includes non-conjugated overhangs and cell penetrating peptide-conjugated overhangs;

wherein the at least one therapeutic agent is selected from the group: siRNA, miRNA, shRNA, asRNA, mRNA, crRNA, tracrRNA, and a RNA vaccine.

2. The nanostructure of claim 1, wherein the at least one cell penetrating peptide and the at least one therapeutic substance are attached to the surface of the nanostructure.

3. The nanostructure of claim 1, wherein the at least one therapeutic substance is capable of gene silencing or gene editing.

4. The nanostructure of claim 1, wherein the nanostructure is capable of penetrating a cell using non-endocytic penetration.

5. The nanostructure of claim 1, wherein the nanostructure includes at least ten nonconjugated single-stranded overhangs for every cell penetrating peptide-conjugated single-stranded overhang.

6. The nanostructure of claim 1, wherein the at least one therapeutic compound is attached to one or more of the non-conjugated overhangs.

7. A method of treating a subject, the method comprising:
providing a nucleic acid nanostructure having:
a DNA or RNA scaffold;
at least one single-stranded nucleic acid staple strand complementary to the scaffold;
at least one positively charged cell penetrating peptide attached to the at least one staple strand; and
at least one therapeutic substance attached to the at least one staple strand;
wherein the nanostructure includes non-conjugated overhangs and cell penetrating peptide-conjugated overhangs;
wherein the at least one therapeutic agent is selected from the group: siRNA, miRNA, shRNA, asRNA, mRNA, crRNA, tracrRNA, and a RNA vaccine; and
administering a therapeutically effective amount of the nucleic acid nanostructure to a subject.

8. The method of claim 7, wherein the method is a method for treating cancer.

9. The method of claim 7, wherein the at least one cell penetrating peptide and the at least one therapeutic substance are attached to the surface of the nanostructure.

10. The method of claim 7, wherein the at least one therapeutic substance is capable of gene silencing or gene editing.

11. The method of claim 7, wherein the nanostructure is capable of penetrating a cell using non-endocytic penetration.

12. The method of claim 7, wherein the method is a method for treating a genetically-related condition.

13. A nucleic acid nanostructure, comprising:
a DNA or RNA scaffold;
at least one single stranded nucleic acid staple strand complementary to the scaffold;
at least one cell penetrating peptide attached to the at least one staple strand; and
at least one therapeutic substance attached to the at least one staple strand;
wherein the at least one cell penetrating peptide is positively charged;
wherein the nanostructure includes non-conjugated overhangs and cell penetrating peptide-conjugated overhangs.

14. The nanostructure of claim 13, wherein the nanostructure includes at least ten non-conjugated single-stranded overhangs for every cell penetrating peptide-conjugated single-stranded overhang.

15. The nanostructure of claim 13, wherein the at least one therapeutic compound is attached to one or more of the non-conjugated overhangs.

16. The nanostructure of claim 13, wherein the at least one therapeutic substance is capable of gene silencing or gene editing.

17. The nanostructure of claim 13, wherein the nanostructure is capable of penetrating a cell using non-endocytic penetration.

18. A method of treating a subject, the method comprising:
providing a nucleic acid nanostructure having:
a DNA or RNA scaffold;
at least one single-stranded nucleic acid staple strand complementary to the scaffold;
at least one positively charged cell penetrating peptide attached to the at least one staple strand; and
at least one therapeutic substance attached to the at least one staple strand;
wherein the nanostructure includes non-conjugated overhangs and cell penetrating peptide-conjugated overhangs; and
administering a therapeutically effective amount of the nucleic acid nanostructure to a subject.

19. The method of claim 18, wherein the at least one therapeutic substance is capable of gene silencing or gene editing.

20. The method of claim 18, wherein the nanostructure is capable of penetrating a cell using non-endocytic penetration.

* * * * *

SEQUENCE LISTING

```
<160> NUMBER OF SEQ ID NOS: 233

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
augccaaaaa cauuaagaat t                                                   21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
uucuuaaugu uuuuggcaut t                                                   21

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ala Arg Val Arg Arg Arg Gly Pro Arg Arg Gly Gly Cys
1               5                   10

<210> SEQ ID NO 4
```

-continued

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Leu Ala Leu Lys Leu Ala Leu Lys Ala Leu Lys Ala Ala Leu Lys
1               5                   10                  15

Leu Ala Cys

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gln Ile Lys Ile Trp Phe Gln Asn Arg Arg Met Lys Trp Lys Lys
1               5                   10                  15

Cys

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctctggttaa cgtgtct                                              17

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaaacgagaa tttaaagtgc cgtttttaag taattc                         36

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaaagaaatc gcctgataaa taagaatct ctggttaacg tgtct                45

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
```
aaaagagaaa atactgagct acaggcgaaa agattctctg gttaacgtgt ct          52

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aaaatatgcg ccgacatact                                              20

<210> SEQ ID NO 11
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaacgaagag aagtatatcc acctcaaaca tcaatctctg gttaacgtgt ct          52

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaacgcatac ggtgtctgga agtcaggact ctggttaacg tgtct                  45

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaacgtaaat tctggctgtc taccgccatt tgtcg                             35

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaagcgcccg ccagctctgg ttaacgtgtc t                                 31

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaaggtgtcc atataagaac gaccgtacag taaatgaatt                          40

<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaattaagga agttcgttgc ggtccacgta ggaatctctg gttaacgtgt ct            52

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aacatcgcca ttaaaaggga cacagagacc ttcat                               35

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aacatttacg agcataccat tacttcaaac tctggttaac gtgtct                   46

<210> SEQ ID NO 19
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaccaagtac cgcaatagcc cggaatagtc ctcattgagg cactctggtt aacgtgtct    59

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aacccataca ctgagtttcg tggctcc                                        27

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aacgagtgct gctctcatta caagcctt                                       28

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aacgggttct gtccatcacg cctctggtta acgtgtct                          38

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aactgacgta ttaaacgggg tcctccctct ctggttaacg tgtct                  45

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aagcctgggt ggttgaacaa cctctggtta acgtgtct                          38

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aagtatttag ttatagcttc tctggttaac gtgtct                            36

<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aagtgtaaca gggcgtaata aaaatacccca gatgaatatg cgcgaactg             49

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aataaagaac ggatgaaagg gaatcgccgt tttag                             35

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aatagaatat aatgcgtagg aagtaccact gctccatgtt ac                             42

<210> SEQ ID NO 29
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aatcaaacaa aaagataacc tcggaataag taagcctctg gttaacgtgt ct                  52

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
acaaacatac ataatcataa taagaaacac gagcgctctg gttaacgtgt ct                  52

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
acaactaaac agcttgatac ccccacgcct ctggttaacg tgtct                          45

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
acaccgcgct caatcgtctg actcgttact ctggttaacg tgtct                          45

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acactaagga acggccagcc actaaagctt ggattctctg gttaacgtgt ct                  52

```
<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acagctggca ttaaagacag ctgcgaattg ggcgc                               35

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
accacattgc ggaatcatat t                                              21

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
accaccatca aaataattc gaaaggctct ctggttaacg tgtct                     45

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
accagcgcac cattcaatag caggattaga acgaggcgca ga                       42

<210> SEQ ID NO 38
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
acccccacga ttaaacgctc aagccagctg gaaggctctg gttaacgtgt ct            52

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
accgttcatg tgtataccaa ataagaaacc caaaactctg gttaacgtgt ct            52

<210> SEQ ID NO 40
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
acgaggcggg ggtaatagta aaacagttct ctggttaacg tgtct            45

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
acgttgtagc tggctcgcct gaattaccct ctggttaacg tgtct            45

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
actatcatgc aaaacatttt cctactaaag gcaaggcaaa ga               42

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agagcaattc aacgcagttg ggttatat                               28

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
agatagcagc taaatcggtt gggtaaagct ctggttaacg tgtct            45

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agatgatggc aatttatcaa actctggtta acgtgtct                    38

<210> SEQ ID NO 46
<211> LENGTH: 52
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agattaacaa tcatttaata ttgattgtat cacctctctg gttaacgtgt ct            52

<210> SEQ ID NO 47
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agcatgtgac gctgttttc acctgaacca caatcctctg gttaacgtgt ct             52

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agcccccgaa taagacgaga atacgtga                                       28

<210> SEQ ID NO 49
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agcgggcctt tgacgattca ccagaagagt agattctctg gttaacgtgt ct            52

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aggaatttag taattttcaa cagacgtttc aggag                               35

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aggaggcgcg attataccaa actctggtta acgtgtct                            38

<210> SEQ ID NO 52
<211> LENGTH: 56
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 52
agggcgagca ctaagtacag agccagggct gcaaggcgat taaggacctg aaagcg      56

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
agggcttacc ggaaatcaat actctggtta acgtgtct                          38

<210> SEQ ID NO 54
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agggtagata tattttctt aatagattta ttaatctctg gttaacgtgt ct           52

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aggtgaacgg tcgcctctgg ttaacgtgtc t                                 31

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agtaaattct atcactctgg ttaacgtgtc t                                 31

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agtagattcg cagtatgaaa tactctggtt aacgtgtct                         39

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ataaagcaaa agcctttaat gctctggtta acgtgtct                              38

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ataacatgtt tgaaggcaga gtcggtgcct tgcatgcctg ca                        42

<210> SEQ ID NO 60
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ataaccgcaa cggcgccagc tattgcccag gaattctctg gttaacgtgt ct             52

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ataatccttt gttaggcaaa gaaggtaa                                        28

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
atacttctta aattcaggct ggagaatata                                      30

<210> SEQ ID NO 63
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
atagcagata aataacaacg cttacgccaa aacgacggcc ag                        42

<210> SEQ ID NO 64
<211> LENGTH: 52
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 64
atcaattagg gataacaaac tagaggcgct cagcactctg gttaacgtgt ct          52

<210> SEQ ID NO 65
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
atcaggtcct ccggcttaga gctctggtta acgtgtct                          38

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
atcatcattt taacctccag cgttcagc                                     28

<210> SEQ ID NO 67
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atcatggaaa ccaaaattcg taaaactctc tggttaacgt gtct                   44

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
atcatttcct tcctgtttga gagtcctgat aatcgcgaac g                      41

<210> SEQ ID NO 69
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
atcgtaaccg tgcaacaact aaaggaatcc tcatagaacc gc                     42

<210> SEQ ID NO 70
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
atgaaaccat cgaattagag ccagctagaa ggagactcct cataag                46

<210> SEQ ID NO 71
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
atgaacggta atcgcattaa attttttgtcg cttct                              35

<210> SEQ ID NO 72
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
atgccggttt aaatgtaata cttttgcgaa aataa                             35

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
atggtcaatt aagactctgg ttaacgtgtc t                                  31

<210> SEQ ID NO 74
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atggttggct agggccgtaa aaaaaccgtg ggcttctctg gttaacgtgt ct           52

<210> SEQ ID NO 75
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
attaattttc ccttttttaat gaaaaacaca aaaggctctg gttaacgtgt ct          52

<210> SEQ ID NO 76
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
attatactac aggaaaggat taagcaaacg agccagtaat aa                              42

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
attattaaga atggtataag tctcatcgac aataaa                                    36

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
attattttga atacttcgct acaacatg                                             28

<210> SEQ ID NO 79
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
attcaaacaa tatgattctc cactcgtaat ttgagctctg gttaacgtgt ct                  52

<210> SEQ ID NO 80
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
attgagtaac tatagaacgc gtcaggaaaa acaacaacat ca                             42

<210> SEQ ID NO 81
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
attgcataat caggaggctt ttaaccctgt ttttcctctg gttaacgtgt ct                  52

<210> SEQ ID NO 82
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
caaatcacca tagggtgaag cataacgaac aaaaacgcaa taataagttt agc    53

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
caacagttgc gggataccaa ctttagcgt    29

<210> SEQ ID NO 84
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
caacatcagc tttccggcac taaatcaaga atcgctctgg ttaacgtgtc t    51

<210> SEQ ID NO 85
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
caactttccc gattcgagaa actctggtta acgtgtct    38

<210> SEQ ID NO 86
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cacaaactga gattctggtt tctctggtta acgtgtct    38

<210> SEQ ID NO 87
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
caccaccaat cagttcaccg aggtaaataa tgaaactctg gttaacgtgt ct    52

<210> SEQ ID NO 88
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
caccaccgat aagatcaaca tattttgtaa agtcactctg gttaacgtgt ct          52

<210> SEQ ID NO 89
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
caccctcaga gccaattcca ctgaatcgcg gaacgctctg gttaacgtgt ct          52

<210> SEQ ID NO 90
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cactacgtga ggccaaacta ttcaatatga ttatcctctg gttaacgtgt ct          52

<210> SEQ ID NO 91
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cagaaaacga aagagataca tcatgattac cgaagctctg gttaacgtgt ct          52

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cagacgaacc aaaacaatag g                                           21

<210> SEQ ID NO 93
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cagactcatc ttttcataat caaaatcgtt tgcc                             34

<210> SEQ ID NO 94
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cagagccgcc acccggtaat attaagaaca gtttgctctg gttaacgtgt ct              52

<210> SEQ ID NO 95
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cagccattat cataaaattc tacgtggcac agacagaatg gc                        42

<210> SEQ ID NO 96
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
cagttaccac ccaggattag tcaagaacca agagtccaaa tccgctgcg                 49

<210> SEQ ID NO 97
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
catatataga gggtgctttc agtttgagag cactactctg gttaacgtgt ct             52

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
catcagtaaa taaagtgtat cggtatta                                        28

<210> SEQ ID NO 99
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cattgacgta ccttactaaa gaagacacgc taatactctg gttaacgtgt ct             52

<210> SEQ ID NO 100
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ccaatcaaac aagaggagaa ggaaccctct ctggttaacg tgtct                     45

<210> SEQ ID NO 101
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 101
ccaccagcag tcacacgacc agcgtactct ctggttaacg tgtct                45

<210> SEQ ID NO 102
<211> LENGTH: 38
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 102
ccaccctgaa gtttgaccat actctggtta acgtgtct                        38

<210> SEQ ID NO 103
<211> LENGTH: 38
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 103
cccaaaaact cgcgcagagg cctctggtta acgtgtct                        38

<210> SEQ ID NO 104
<211> LENGTH: 35
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 104
ccctcaacgg ccttctgttt ccacaacagg gttga                           35

<210> SEQ ID NO 105
<211> LENGTH: 35
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 105
cccttttaac attaccaata agtgtagaaa taatt                           35

<210> SEQ ID NO 106
<211> LENGTH: 52
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 106
ccggttgcat agcgaatttc aacgggagat ggtttctctg gttaacgtgt ct        52

<210> SEQ ID NO 107
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cctcaaattt taattcgagc tctctggtta acgtgtct                    38

<210> SEQ ID NO 108
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cctcagaatg gcttagagcc actctggtta acgtgtct                    38

<210> SEQ ID NO 109
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cctgactcag aagctcattt gaccgaggag ttaccctctg gttaacgtgt ct    52

<210> SEQ ID NO 110
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cctggccggg aaacctgtcg ttacagagct ctggttaacg tgtct            45

<210> SEQ ID NO 111
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cctttaaagt attcaaacaa ctctggttaa cgtgtct                     37

<210> SEQ ID NO 112
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cgaaccttcg gaacgaacgg tatcggaacg aaaggctctg gttaacgtgt ct    52

<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
cgacggcgga tccgttcccc agaacctctg gttaacgtgt ct                        42

<210> SEQ ID NO 114
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cgcaacttct agagaggaaa aagggattct ctggttaacg tgtct                     45

<210> SEQ ID NO 115
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cgccaccggc cggaccagta gccaaagagg gaagcctctg gttaacgtgt ct             52

<210> SEQ ID NO 116
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cgctgagtgg aaatacctac agctaaacct ctggttaacg tgtct                     45

<210> SEQ ID NO 117
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cggatatatt cagtttatta gctctggtta acgtgtct                             38

<210> SEQ ID NO 118
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cggcaaaatc ccttcgttaa tctctggtta acgtgtct                             38

<210> SEQ ID NO 119

```
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
cggtcaatca agaggtgtac ttcagaacct ctggttaacg tgtct                    45

<210> SEQ ID NO 120
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cgtaacccgc cgcgcttaat gcgccgct                                       28

<210> SEQ ID NO 121
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cgtttgcgta gcgctttatc cagagcctat cccaactctg gttaacgtgt ct            52

<210> SEQ ID NO 122
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ctattataca gtgcccagag cctctggtta acgtgtct                            38

<210> SEQ ID NO 123
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ctgagtatag ctgagagcga gcgaacgtag agccgctctg gttaacgtgt ct            52

<210> SEQ ID NO 124
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctggagctct gagagctgat ggataaccat aaaagctctg gttaacgtgt ct            52

<210> SEQ ID NO 125
<211> LENGTH: 45
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cttatcctaa tttaataccg agctattact ctggttaacg tgtct                    45

<210> SEQ ID NO 126
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cttattatag tttggtagaa aaccctcagt tagcg                               35

<210> SEQ ID NO 127
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cttgcctaat caaccggaat tctctggtta acgtgtct                            38

<210> SEQ ID NO 128
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ctttaataca gtaaaacaaa actctggtta acgtgtct                            38

<210> SEQ ID NO 129
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ctttgcctaa caaccacgtt gatcatacta gtagt                               35

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gaaaaatttg caacgatccc c                                              21

<210> SEQ ID NO 131
<211> LENGTH: 52
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 131
gaaacagtca agaacagtac cttaacgtga acgaactctg gttaacgtgt ct            52

<210> SEQ ID NO 132
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gaaattattc attagatttt tctctggtta acgtgtct                            38

<210> SEQ ID NO 133
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gaacaagtga cggggaagcg cgaaacaagt tgttcctggc tcctctggtt aacgtgtct    59

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gaacgtgggg agccgaaaga g                                              21

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gaactggttc gcaaagcatt                                                20

<210> SEQ ID NO 136
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gaatcaaacc ggaaccgtat atttaattac gtcaactctg gttaacgtgt ct            52

<210> SEQ ID NO 137
<211> LENGTH: 52
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 137
gaatcagaac gtggtagagc tagtccacta ccttactctg gttaacgtgt ct            52

<210> SEQ ID NO 138
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gaatcctaga ggcatgtgtc gaagcataaa gtgta                               35

<210> SEQ ID NO 139
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gaattataat cgtcccgtgt gcctttacat tgaggctctg gttaacgtgt ct            52

<210> SEQ ID NO 140
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gacaacagga ctaatccagt cctgagagat gcagactctg gttaacgtgt ct            52

<210> SEQ ID NO 141
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gacgacgaga acaagcaagc cgtcgagata cgagccggaa atccg                    45

<210> SEQ ID NO 142
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gagaatacta aagtccctca gatagcgtga atccctctg gttaacgtgt ct             52

<210> SEQ ID NO 143
<211> LENGTH: 28
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 143
gagatggaac agttaatgcc gtaacaaa                                              28

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gagggaactt gagctaagaa c                                                     21

<210> SEQ ID NO 145
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gagggtagaa cgcgagaaaa cagaagagct ctggttaacg tgtct                           45

<210> SEQ ID NO 146
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gaggtgatat ttacattggc agagcacgct ctggttaacg tgtct                           45

<210> SEQ ID NO 147
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gataaaagat ctaccgtctg gtgcggaagt tatctctctg gttaacgtgt ct                   52

<210> SEQ ID NO 148
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gataggtccg tcggatattc actctggtta acgtgtct                                   38

<210> SEQ ID NO 149
<211> LENGTH: 38
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 149
gattcccgaa ataaataat actctggtta acgtgtct                                    38

<210> SEQ ID NO 150
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gatttagatt gtataaaaaa acaccagtgc aagcctagcg agtctttac                       49

<210> SEQ ID NO 151
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gcaaactcga ttggccttgg tcataaatga accag                                     35

<210> SEQ ID NO 152
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gcaagcgctc actgcccgct tagactttct ctggttaacg tgtct                          45

<210> SEQ ID NO 153
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcaatagcta tcttaagact cctctggtta acgtgtct                                  38

<210> SEQ ID NO 154
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gcaccgtgga accgcagtgc cttgagtatc tgaaacatga aa                             42

<210> SEQ ID NO 155
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gcattagtct tctgacctaa aagaatccct ctggttaacg tgtct                    45

<210> SEQ ID NO 156
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gccccagact cacattaatt gtccattact ctggttaacg tgtct                    45

<210> SEQ ID NO 157
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gccggcgagc gggattttga cctgcaacta tcaaactctg gttaacgtgt ct            52

<210> SEQ ID NO 158
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gcgaaagtgc agggtcagct tataatactt aaatcctctg gttaacgtgt ct            52

<210> SEQ ID NO 159
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gcgacattca accgagagag actctggtta acgtgtct                            38

<210> SEQ ID NO 160
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gcgaggcata tttaaggcgt taccttgcct ctggttaacg tgtct                    45

<210> SEQ ID NO 161
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gcggtcaaag ttttggccca cacaccagct ctggttaacg tgtct        45

<210> SEQ ID NO 162
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gctaaaggtg aattatcacc gagcgacact ctggttaacg tgtct        45

<210> SEQ ID NO 163
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gctgaaaaaa ttaagcctca ggaaaggcct ctggttaacg tgtct        45

<210> SEQ ID NO 164
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gctttgaacc atcggatagt tctttaggta acattctctg gttaacgtgt ct        52

<210> SEQ ID NO 165
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ggaaccgtgc caaggggcct ccaagttaca aaaaggaaga ttagggcgag catttt        56

<210> SEQ ID NO 166
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ggaagaagtc atactttgct catcattacc gcgccactta a        41

<210> SEQ ID NO 167
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ggaagcccga gaattgccag aatagtaaac gggcactctg gttaacgtgt ct            52

<210> SEQ ID NO 168
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ggaagggtgc tttcaatgga tggcggtcaa acagactctg gttaacgtgt ct            52

<210> SEQ ID NO 169
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ggccgctcgt caccgtttgc gcagggtgcg tttac                              35

<210> SEQ ID NO 170
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gggcgatttg gggttggctg atagaaccct tctttgggta acccaggcgc a            51

<210> SEQ ID NO 171
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gggtacccgc cattgtaaac gatgtaccct ctggttaacg tgtct                   45

<210> SEQ ID NO 172
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ggtattccat ttgggatagc actctggtta acgtgtct                           38

<210> SEQ ID NO 173
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ggtcagacca acaggtttca tgcaacatca caagactctg gttaacgtgt ct        52

<210> SEQ ID NO 174
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ggtcgacgtt gggagtataa ggaaaagcct ctggttaacg tgtct              45

<210> SEQ ID NO 175
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gtaatggatc tccacggttt aagttaaact ctggttaacg tgtct              45

<210> SEQ ID NO 176
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gttagaacct accaagtgcc actctggtta acgtgtct                      38

<210> SEQ ID NO 177
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gttgagtagt acaacggaga tatctttgct ctggttaacg tgtct              45

<210> SEQ ID NO 178
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gttggcagag tagaagaact caccgagtct ctggttaacg tgtct              45

<210> SEQ ID NO 179
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gtttagtttc cttaatcaac aatagatagg gacgagcgga gt                 42

<210> SEQ ID NO 180
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gtttgatggg tgccaattcc actgtgtgaa attgttatgg gatt            44

<210> SEQ ID NO 181
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
taacgatgaa aggatctgcc agtagccaag ctattctctg gttaacgtgt ct    52

<210> SEQ ID NO 182
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
taagaattac cagtaaatca actacaatgt tttcatcggc at              42

<210> SEQ ID NO 183
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
taagccccat acatctctgg ttaacgtgtc t                          31

<210> SEQ ID NO 184
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
taagtttgtt ttaaatatgc ataattgcct ctggttaacg tgtct           45

<210> SEQ ID NO 185
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
taatcagaag gcaccaacct actctggtta acgtgtct                   38

<210> SEQ ID NO 186
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 186
taatcattgt gaattattaa actctggtta acgtgtct                          38

<210> SEQ ID NO 187
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 187
taatgcatgt aaatgactac cctctggtta acgtgtct                          38

<210> SEQ ID NO 188
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 188
tacataacgc caaattcacc gctctggtta acgtgtct                          38

<210> SEQ ID NO 189
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 189
taggccgagg tgcgctggcc tctggttaac gtgtct                            36

<210> SEQ ID NO 190
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 190
tataacgaag aaagccctaa agactccatc aacttctctg gttaacgtgt ct          52

<210> SEQ ID NO 191
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 191
tatatttaaa gcggctctgg ttaacgtgtc t                                 31

```
<210> SEQ ID NO 192
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tatcccatcc taattgaccc tgcaatgcct ctggttaacg tgtct              45

<210> SEQ ID NO 193
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tatcgcgtgc tttaaatgtt tagactggaa ccgcc                        35

<210> SEQ ID NO 194
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tatgtgaaag aagaaaacaa taaattgcta aaacactctg gttaacgtgt ct     52

<210> SEQ ID NO 195
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tcaaagcatt cattccaata ctcaactaag ttgcactctg gttaacgtgt ct     52

<210> SEQ ID NO 196
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tcaataggct ttcgttttca cctgtagc                                28

<210> SEQ ID NO 197
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tcaatagtga atttagacaa aattgagcca cggaactctg gttaacgtgt ct     52

<210> SEQ ID NO 198
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tcagagacaa atccaatcgc aatcaaaact ctggttaacg tgtct            45

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tcagataaaa atcaaacgtc acca                                   24

<210> SEQ ID NO 200
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tcataggaaa caaggctcat ttattcctct ggtcactctg gttaacgtgt ct    52

<210> SEQ ID NO 201
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tcattccaac agttaccgga actctggtta acgtgtct                    38

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tccaaattac tagacaacgc t                                      21

<210> SEQ ID NO 203
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tccttttaga gccgagtctc tactaacgcc gaaatctctg gttaacgtgt ct    52

<210> SEQ ID NO 204
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tctttccagt ttcacgacag tatcggcccc tgttt                                35

<210> SEQ ID NO 205
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tctttcctga atctggtttt gccaaatcaa cccctgccta ttcccgact                 49

<210> SEQ ID NO 206
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tctttgatga ggaagcaaag aactctggtt aacgtgtct                            39

<210> SEQ ID NO 207
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tgaacacaat atatccgaca acgccattga gctcgaattc gta                      43

<210> SEQ ID NO 208
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tgagcaagtg aataaaataa gcgtcaaaat tgacgctctg gttaacgtgt ct            52

<210> SEQ ID NO 209
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tgaggctaca gcatgccaac gcagtgagga gcaacctctg gttaacgtgt ct            52

<210> SEQ ID NO 210
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 210
tgcgattagt tttagaggct g                                              21

<210> SEQ ID NO 211
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tgctgaagaa caatattacc gtacgccact ctggttaacg tgtct                    45

<210> SEQ ID NO 212
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tgtccaggtg ccggtcatag gctggtagtt tttactctgg ttaacgtgtc t             51

<210> SEQ ID NO 213
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
tgtttaaaat aaacaattga gggatgtgtt ttcccagtca cggacagat                49

<210> SEQ ID NO 214
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ttaattatac cttttgttta gattatttaa tttgcctctg gttaacgtgt ct            52

<210> SEQ ID NO 215
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
ttagacaaac actcttgtat ctagcccgga cgttgctctg gttaacgtgt ct            52

<210> SEQ ID NO 216
<211> LENGTH: 52
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 216
ttagagaagg aggttaaagc ccaggtagaa atcctctctg gttaacgtgt ct            52

<210> SEQ ID NO 217
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ttagcaactc agagttgatg acagtcagag ataggctctg gttaacgtgt ct            52

<210> SEQ ID NO 218
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ttagccggcg gggtatggct tccaccacct ctggttaacg tgtct                   45

<210> SEQ ID NO 219
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ttcaggtttt tacatcggga gtgatgaact ctggttaacg tgtct                   45

<210> SEQ ID NO 220
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ttcatgaccg ttgtagcaaa tctctggtta acgtgtct                           38

<210> SEQ ID NO 221
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ttcgacagtg ggaaattgac cattagcaag gtggc                              35

<210> SEQ ID NO 222
<211> LENGTH: 52
<212> TYPE: DNA
<213> ORGANISM: Artificial Sequence
<220> FEATURE:
```

-continued

<223> OTHER INFORMATION: Description of Artificial Sequence: Synthetic
     oligonucleotide

<400> SEQUENCE: 222
ttctgtatca tttcattgct tgcacgtaag tattactctg gttaacgtgt ct                52

<210> SEQ ID NO 223
<211> LENGTH: 47
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 223
ttctgtatcc gctcactaat gaggtaatgc ctctggttaa cgtgtct                     47

<210> SEQ ID NO 224
<211> LENGTH: 52
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 224
ttgaaaaata atcacaaata ttgaataaag caaatctctg gttaacgtgt ct                52

<210> SEQ ID NO 225
<211> LENGTH: 39
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 225
ttgctgaaaa ttcataatta acctctggtt aacgtgtct                              39

<210> SEQ ID NO 226
<211> LENGTH: 43
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 226
ttgctgatcg cacaataggt gagagtctct ggttaacgtg tct                         43

<210> SEQ ID NO 227
<211> LENGTH: 45
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 227
tttaaaatca acattaaatg ttaaattact ctggttaacg tgtct                       45

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
tttgaatcat ttaatattag t                                          21

<210> SEQ ID NO 229
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tttgagaatt tttaccttta tgaaacaatg ttagcctctg gttaacgtgt ct         52

<210> SEQ ID NO 230
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tttgcgggcc gccaagtaag caaatctaat aaatcctctg gttaacgtgt ct         52

<210> SEQ ID NO 231
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ttttcaccgc ggggacaacg cgttgaaa                                    28

<210> SEQ ID NO 232
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ttttcatctg tagcggtcat tctctggtta acgtgtct                         38

<210> SEQ ID NO 233
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tttttaacat tgccaacgcc agaaggagag ttgaactctg gttaacgtgt ct         52
```